United States Patent
Mahmoodian et al.

(10) Patent No.: US 11,045,589 B2
(45) Date of Patent: Jun. 29, 2021

(54) 4% TRISODIUM CITRATE SOLUTION FOR USE AS A CATHETER LOCK SOLUTION

(71) Applicant: Becton, Dickinson and Company, Franklin Lakes, NJ (US)

(72) Inventors: Roza Mahmoodian, New York, NY (US); Suzanne Ferreri, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 29 days.

(21) Appl. No.: 16/137,946

(22) Filed: Sep. 21, 2018

(65) Prior Publication Data

US 2019/0091379 A1    Mar. 28, 2019

Related U.S. Application Data

(60) Provisional application No. 62/561,859, filed on Sep. 22, 2017.

(51) Int. Cl.
| | |
|---|---|
| *A61L 33/00* | (2006.01) |
| *A61L 29/16* | (2006.01) |
| *A61L 29/14* | (2006.01) |
| *A61M 25/00* | (2006.01) |

(52) U.S. Cl.
CPC .......... *A61L 33/0011* (2013.01); *A61L 29/14* (2013.01); *A61L 29/16* (2013.01); *A61L 2300/21* (2013.01); *A61L 2300/404* (2013.01); *A61L 2300/42* (2013.01); *A61M 2025/0019* (2013.01)

(58) Field of Classification Search
CPC ...... A61L 29/16; A61L 29/14; A61L 33/0011; A61L 2300/21; A61L 23/42
See application file for complete search history.

(56) References Cited

U.S. PATENT DOCUMENTS

| | | | |
|---|---|---|---|
| 5,032,615 A | 7/1991 | Ward et al. | |
| 5,667,963 A | 9/1997 | Smith et al. | |
| 5,688,516 A | 11/1997 | Raad et al. | |
| 6,166,007 A | 12/2000 | Sodemann | |
| 6,187,768 B1 | 2/2001 | Welle et al. | |
| 6,262,038 B1 | 7/2001 | Pierce et al. | |
| 6,350,251 B1 | 2/2002 | Prosl et al. | |
| 6,423,706 B2 | 7/2002 | Sodemann | |
| 6,498,157 B2 | 12/2002 | Sodemann | |
| 6,569,852 B1 | 5/2003 | Sodemann | |
| 6,679,870 B1 | 1/2004 | Finch et al. | |
| 6,685,694 B2 | 2/2004 | Finch et al. | |
| 6,958,049 B1 | 10/2005 | Ash | |
| 7,132,413 B1 | 11/2006 | Pfirrmann | |
| 7,696,182 B2 | 4/2010 | Prosl | |
| 7,704,935 B1 | 4/2010 | Davis et al. | |
| 7,732,486 B2 | 6/2010 | Arata | |
| 7,749,529 B2 | 7/2010 | Ash et al. | |
| 7,763,297 B2 | 7/2010 | Arata | |
| 7,803,407 B2 | 9/2010 | Arata | |
| 7,820,651 B2 | 10/2010 | Herdeis et al. | |
| 7,833,215 B2 | 11/2010 | Appling | |
| 7,884,132 B2 | 2/2011 | Tolwani et al. | |
| 8,162,899 B2 | 4/2012 | Tennican | |
| 8,226,971 B2 | 7/2012 | Ash et al. | |
| 8,541,393 B2 | 9/2013 | Prosl | |
| 8,622,995 B2 | 1/2014 | Ziebol et al. | |
| 8,622,996 B2 | 1/2014 | Ziebol et al. | |
| 8,703,739 B2 | 4/2014 | Kimura et al. | |
| 8,709,342 B2 | 4/2014 | Raad | |
| 8,747,911 B2 | 6/2014 | Gupta et al. | |
| 8,795,240 B2 | 8/2014 | Chelak | |
| 8,845,593 B2 | 9/2014 | Anderson et al. | |
| 8,864,742 B2 | 10/2014 | Cary | |
| 9,011,897 B2 | 4/2015 | Ash et al. | |
| 9,212,339 B2 | 12/2015 | Laugeman | |
| 9,339,036 B2 | 5/2016 | Prosl | |
| 9,427,498 B2 | 8/2016 | Mills et al. | |
| 9,433,209 B2 | 9/2016 | Mills et al. | |
| 9,457,002 B2 | 10/2016 | Raad et al. | |
| 9,555,116 B2 | 1/2017 | Folan | |
| 9,649,411 B2 | 5/2017 | Hoang | |
| 2003/0144362 A1 | 7/2003 | Utterberg et al. | |
| 2003/0175323 A1 | 9/2003 | Utterberg et al. | |
| 2003/0185777 A1* | 10/2003 | Banowski | A61K 8/26 424/66 |
| 2004/0092890 A1 | 5/2004 | Ash | |
| 2005/0131356 A1 | 6/2005 | Ash et al. | |
| 2005/0215978 A1 | 9/2005 | Ash | |
| 2006/0063835 A1 | 3/2006 | De Paoli Ambrosi | |

(Continued)

FOREIGN PATENT DOCUMENTS

| | | |
|---|---|---|
| CA | 2307560 A1 | 5/1999 |
| CA | 2414481 A1 | 1/2002 |

(Continued)

OTHER PUBLICATIONS

TERUMOBCT BD lock solution sodium citrate 4% w/v anticoagulant solution USP, 1978.*
Sigma-Aldrich, Sodium citrate tribasic dehydrate (citric acid trisodium salt dehydrate, Trisodium citrate dihydrate), obtained online Nov. 2, 2020.*
Barbaric et al., "Role of Hydrochloric Acid in the Treatment of Central Venous Catheter Infections in Children with Cancer", Cancer, 2004, vol. 101, No. 8, pp. 1866-1872.
Levesque et al., "Stability of Trisodium Citrate 4.0% and 46.7% in Polyvinyl Chloride Syringes", CJHP, 2001, vol. 54, No. 4, pp. 264-268.
Shulman et al., "Use of Hydrochloric Acid to Clear Obstructed Central Venous Catheters", Journal of Parenteral and Enteral Nutrition, 1988, vol. 12, No. 5, pp. 509-510.

(Continued)

*Primary Examiner* — Mina Haghighatian
(74) *Attorney, Agent, or Firm* — The Webb Law Firm

(57) ABSTRACT

Provided herein are catheter lock solutions having anticoagulation and antimicrobial properties, the catheter lock solutions including citrate salts. The citrate salt can be trisodium citrate, and the catheter lock solution can further include a diluted acid for adjusting the pH of the catheter lock solution.

10 Claims, 12 Drawing Sheets

(56) References Cited

U.S. PATENT DOCUMENTS

| | | |
|---|---|---|
| 2006/0094690 A1 | 5/2006 | Prosl |
| 2006/0177477 A1 | 8/2006 | Ash et al. |
| 2007/0202177 A1 | 8/2007 | Hoang |
| 2007/0244449 A1 | 10/2007 | Najafi et al. |
| 2007/0281891 A1 | 12/2007 | Wieslander |
| 2008/0279907 A1 | 11/2008 | Ash et al. |
| 2008/0311231 A1 | 12/2008 | Modak et al. |
| 2010/0010086 A1 | 1/2010 | Ash et al. |
| 2010/0055086 A1 | 3/2010 | Raad |
| 2010/0087788 A1 | 4/2010 | Rosenblatt et al. |
| 2010/0106103 A1 | 4/2010 | Ziebol et al. |
| 2010/0191219 A1 | 7/2010 | Gupta et al. |
| 2010/0249747 A1 | 9/2010 | Mills et al. |
| 2010/0318040 A1* | 12/2010 | Kelley, III ......... A61K 9/0019 604/265 |
| 2010/0331277 A1 | 12/2010 | Prosl |
| 2011/0201692 A1 | 8/2011 | Raad |
| 2011/0208159 A1 | 8/2011 | Cary |
| 2011/0311602 A1 | 12/2011 | Mills et al. |
| 2012/0034319 A1* | 2/2012 | Gupta ............... A61L 29/14 424/666 |
| 2012/0277314 A1 | 11/2012 | Ash et al. |
| 2012/0282351 A1 | 11/2012 | Najafi et al. |
| 2012/0289591 A1 | 11/2012 | Folan |
| 2012/0296284 A1 | 11/2012 | Anderson et al. |
| 2013/0053439 A1 | 2/2013 | Kirschner |
| 2013/0138083 A1 | 5/2013 | Tennican |
| 2013/0172260 A1 | 7/2013 | Polaschegg |
| 2013/0178526 A1 | 7/2013 | Ash et al. |
| 2013/0183363 A1 | 7/2013 | Polaschegg |
| 2013/0184679 A1 | 7/2013 | Ziebol et al. |
| 2013/0190724 A1 | 7/2013 | Polaschegg |
| 2013/0199946 A1 | 8/2013 | Tennican |
| 2013/0274686 A1 | 10/2013 | Ziebol et al. |
| 2014/0102299 A1 | 4/2014 | Wilt et al. |
| 2014/0112828 A1 | 4/2014 | Grant et al. |
| 2014/0217020 A1 | 8/2014 | Meyer et al. |
| 2014/0220617 A1 | 8/2014 | Yung et al. |
| 2014/0228327 A1 | 8/2014 | Raad |
| 2014/0243323 A1 | 8/2014 | Prosl |
| 2014/0248600 A1 | 9/2014 | Hertz et al. |
| 2014/0275264 A1 | 9/2014 | Consalo et al. |
| 2015/0018774 A1 | 1/2015 | Anderson et al. |
| 2015/0148287 A1 | 5/2015 | Woo et al. |
| 2015/0151025 A1 | 6/2015 | Gupta et al. |
| 2016/0120898 A1 | 5/2016 | Elliott |
| 2016/0199329 A1 | 7/2016 | Uddin |
| 2016/0213818 A1 | 7/2016 | Hoang |
| 2016/0331870 A1 | 11/2016 | Xie et al. |
| 2017/0128629 A1 | 5/2017 | Prosl |
| 2017/0232153 A1* | 8/2017 | Babu ............... A61L 2/0088 422/28 |

FOREIGN PATENT DOCUMENTS

| | | |
|---|---|---|
| CA | 2550004 A1 | 12/2005 |
| CA | 2597055 A1 | 8/2006 |
| CA | 2601031 A1 | 10/2006 |
| CA | 2643140 A1 | 9/2007 |
| CA | 2643804 A1 | 9/2007 |
| CA | 2741890 A1 | 5/2010 |
| CA | 2807362 A1 | 2/2012 |
| CA | 2852965 A1 | 4/2013 |
| CA | 2929554 A1 | 5/2015 |
| CA | 2931460 A1 | 5/2015 |
| CA | 2934538 A1 | 6/2015 |
| DE | 102005002643 A1 | 7/2006 |
| DE | 60311958 T2 | 11/2007 |
| DE | 602004008878 T2 | 6/2008 |
| DE | 102011114459 A1 | 3/2013 |
| EP | 0953320 A2 | 11/1999 |
| EP | 1017427 A1 | 11/1999 |
| EP | 1089738 A1 | 4/2001 |
| EP | 1107807 | 6/2001 |
| EP | 1245247 A1 | 10/2002 |
| EP | 1284780 | 2/2003 |
| EP | 1312008 | 5/2003 |
| EP | 1348451 A1 | 10/2003 |
| EP | 1369136 A1 | 12/2003 |
| EP | 1374905 A1 | 1/2004 |
| EP | 1682196 | 7/2006 |
| EP | 1688154 A1 | 8/2006 |
| EP | 1813293 A2 | 8/2007 |
| EP | 1814562 | 8/2007 |
| EP | 1882476 A1 | 1/2008 |
| EP | 2366397 A1 | 9/2011 |
| EP | 2600927 | 6/2013 |
| EP | 2731658 | 5/2014 |
| EP | 2882433 | 6/2015 |
| EP | 2999464 | 3/2016 |
| EP | 3088013 A | 11/2016 |
| EP | 3113621 | 1/2017 |
| GB | 2502291 A | 11/2013 |
| WO | 9015612 A1 | 12/1990 |
| WO | 9638136 A1 | 5/1996 |
| WO | 9629867 A2 | 10/1996 |
| WO | 9635416 A1 | 11/1996 |
| WO | 9636227 A1 | 11/1996 |
| WO | 9724431 A1 | 7/1997 |
| WO | 9903526 A1 | 1/1999 |
| WO | 9910017 A1 | 3/1999 |
| WO | 9934852 A1 | 7/1999 |
| WO | 0050016 A2 | 8/2000 |
| WO | 0072906 A1 | 12/2000 |
| WO | 0205873 A2 | 1/2001 |
| WO | 0128598 A2 | 4/2001 |
| WO | 0149296 A1 | 7/2001 |
| WO | 0153330 A2 | 7/2001 |
| WO | 0154736 A2 | 8/2001 |
| WO | 0185249 A1 | 11/2001 |
| WO | 0197881 A1 | 12/2001 |
| WO | 02067788 A1 | 9/2002 |
| WO | 02082907 A1 | 10/2002 |
| WO | 02087560 A1 | 11/2002 |
| WO | 03097116 A1 | 11/2003 |
| WO | 2004030715 A1 | 4/2004 |
| WO | 2004041343 A1 | 5/2004 |
| WO | 2004075944 A2 | 9/2004 |
| WO | 2004103426 A1 | 12/2004 |
| WO | 2004104019 A2 | 12/2004 |
| WO | 2004108091 A2 | 12/2004 |
| WO | 2004108093 A2 | 12/2004 |
| WO | 2005023233 A2 | 3/2005 |
| WO | 2005027993 A2 | 3/2005 |
| WO | 2005092421 A1 | 10/2005 |
| WO | 2006029255 A2 | 3/2006 |
| WO | 2006029278 A2 | 3/2006 |
| WO | 2006029351 A2 | 3/2006 |
| WO | 2006062846 A2 | 5/2006 |
| WO | 2006049813 A2 | 6/2006 |
| WO | 2006062835 A2 | 6/2006 |
| WO | 2006130629 A2 | 7/2006 |
| WO | 2006099359 A2 | 9/2006 |
| WO | 2006107944 A2 | 10/2006 |
| WO | 2006112782 A1 | 10/2006 |
| WO | 2006115652 A1 | 11/2006 |
| WO | 2006135854 A2 | 12/2006 |
| WO | 2007025312 A2 | 3/2007 |
| WO | 2007027859 A1 | 3/2007 |
| WO | 2007035911 A1 | 3/2007 |
| WO | 2007100776 A2 | 9/2007 |
| WO | 2007101064 A2 | 9/2007 |
| WO | 2007137056 A2 | 11/2007 |
| WO | 2007139844 A2 | 12/2007 |
| WO | 2007142919 A2 | 12/2007 |
| WO | 2007142967 A2 | 12/2007 |
| WO | 2008011048 A2 | 1/2008 |
| WO | 2008011980 A1 | 1/2008 |
| WO | 2008019083 A2 | 2/2008 |
| WO | 2008036134 A2 | 3/2008 |
| WO | 2008043081 A2 | 4/2008 |
| WO | 2008057773 A2 | 5/2008 |
| WO | 2008060380 A2 | 5/2008 |

(56) References Cited

FOREIGN PATENT DOCUMENTS

| | | | |
|---|---|---|---|
| WO | 2008076407 | A2 | 6/2008 |
| WO | 2008076706 | A2 | 6/2008 |
| WO | 2008076708 | A2 | 6/2008 |
| WO | 2008092006 | A2 | 7/2008 |
| WO | 2008133646 | A1 | 11/2008 |
| WO | 2008140974 | A1 | 11/2008 |
| WO | 2009002474 | A1 | 12/2008 |
| WO | 2009016504 | A2 | 2/2009 |
| WO | 2009045454 | A1 | 4/2009 |
| WO | 2009048759 | A1 | 4/2009 |
| WO | 2009085317 | A1 | 7/2009 |
| WO | 2009085318 | A1 | 7/2009 |
| WO | 2009105484 | A1 | 8/2009 |
| WO | 2009140215 | A2 | 11/2009 |
| WO | 2009142760 | A1 | 11/2009 |
| WO | 2010047830 | A2 | 4/2010 |
| WO | 2010056836 | A1 | 5/2010 |
| WO | 2010062589 | A2 | 6/2010 |
| WO | 2010080830 | A1 | 7/2010 |
| WO | 2010088192 | A1 | 8/2010 |
| WO | 2010110908 | A2 | 9/2010 |
| WO | 2010144674 | A2 | 12/2010 |
| WO | 2011025891 | A2 | 3/2011 |
| WO | 2011061237 | A1 | 5/2011 |
| WO | 2011063928 | A2 | 6/2011 |
| WO | 2011063928 | A2 | 9/2011 |
| WO | 2012018437 | A1 | 2/2012 |
| WO | 2012034032 | A2 | 3/2012 |
| WO | 2012167068 | A1 | 12/2012 |
| WO | 2012167084 | A1 | 12/2012 |
| WO | 2013009998 | A2 | 1/2013 |
| WO | 2013032464 | A1 | 3/2013 |
| WO | 2013049033 | A1 | 4/2013 |
| WO | 2013049626 | A1 | 4/2013 |
| WO | 2013050462 | A1 | 4/2013 |
| WO | 2013082187 | A1 | 6/2013 |
| WO | 2013090701 | A1 | 6/2013 |
| WO | 2013107443 | A1 | 7/2013 |
| WO | 2013116702 | A1 | 8/2013 |
| WO | 2014004498 | A1 | 1/2014 |
| WO | 2014092747 | A1 | 6/2014 |
| WO | 2014120247 | A1 | 8/2014 |
| WO | 2014121166 | A1 | 8/2014 |
| WO | 2014143600 | A1 | 9/2014 |
| WO | 2014155147 | A2 | 10/2014 |
| WO | 2013177622 | A1 | 11/2014 |
| WO | 2014177656 | A1 | 11/2014 |
| WO | 2014189392 | A1 | 11/2014 |
| WO | 2015033024 | A1 | 3/2015 |
| WO | 2015048381 | A1 | 4/2015 |
| WO | 2015057170 | A1 | 4/2015 |
| WO | 2015061493 | A1 | 4/2015 |
| WO | 2015077798 | A1 | 5/2015 |
| WO | 2015089421 | A1 | 6/2015 |
| WO | 2015096614 | A1 | 7/2015 |
| WO | 2015136366 | A1 | 9/2015 |
| WO | 2016063278 | A1 | 4/2016 |
| WO | 2017019499 | A1 | 2/2017 |
| WO | 2017079589 | A1 | 5/2017 |
| WO | 2017139224 | A1 | 8/2017 |

OTHER PUBLICATIONS

Takla et al., "Effectiveness of a 30% ethanol/4% trisodium citrate locking solution in preventing biofilm formation by organisms causing haemodialysis catheter-related infections", Journal of Antimicrobial Chemotherapy, 2008, vol. 62, No. 5, pp. 1024-1026.

Ash et al. "Concentrated Sodium Citrate (23%) for Catheter Lock", Hemodial Int., 2000, pp. 22-31, vol. 4.

Ash. "Advances in Locking Solutions", Endovascular Today, 2010, pp. 66-72.

Bevilacqua et al. "Comparison of Trisodium Citrate and Heparin as Catheter-Locking Solution in Hemodialysis Patients", J Bras Nefrol, 2011, pp. 68-73, vol. 33:1.

Bohler et al. "Reduction of Granulocyte Activation During Hemodialysis with Regional Citrate Anticoagulation: Dissociation of Complement Activation and Neutropenia from Neutrophil Degranulation", J. Am. Soc. Nephrol, 1996, pp. 234-241, vol. 7.

Boyce. "Prevention of Central Line-Associated Bloodstream Infections in Hemodialysis Patients", Infection Control and Hospital Epidemiology, 2012, pp. 936-944, vol. 33.

Branson et al. "Efficacy of 1.4 Percent Sodium Citrate in Maintaining Arterial Catheter Patency in Patients in a Medical ICU", Chest, 1993, pp. 882-885, vol. 103.

Charney et al. "Cardiac Arrest After Hypertonic Citrate Anticoagulation for Chronic Hemodialysis", ASAIO Trans, 1990, pp. M217-219, vol. 36:3.

Davenport. "Why Do Hypertonic Citrate Locks Lead to Dialysis Catheter Malfunction; More Than a Weighty Problem?", Nephrol Dial Transplant, 2012, pp. 2621-2624 vol. 27.

Davenport et al. "Citrate Anticoagulation for Continuous Renal Replacement Therapy (CRRT) in Patients with Acute Kidney Injury Admitted to the Intensive Care Unit", NDT Plus, 2009, pp. 439-447, vol. 2.

Grudzinski et al. "Sodium Citrate 4% Locking Solution for Central Venous Dialysis Catheters—an Effective, More Cost-Efficient Alternative to Heparin", Nephrol Dial Transplant, 2007, pp. 471-476, vol. 22.

Hermite et al. "Sodium Citrate Versus Saline Catheter Locks for Non-Tunneled Hemodialysis Central Venous Catheters in Critically Ill Adults: A Randomized Controlled Trial", Intensive Care Med, 2012, pp. 279-285, vol. 38.

Flanigan et al. "Regional Hemodialysis Anticoagulation: Hypertonic Tri-Sodium Citrate or Anticoagulant Citrate Dextrose-A", Am. J. Kidney Dis. 1996, pp. 519-524, vol. 27:4.

Hesse et al. "Experimental Investigations on Dissolution of Incrustations on the Surface of Catheters", Urol Int. 1989, pp. 364-369, vol. 44.

Lok et al. "Trisodium Citrate 4%—An Alternative to Heparin Capping of Haemodialysis Catheters", Nephrol Dial Transplant, 2007, pp. 477-483, vol. 22.

Luo et al. "Vascular Catheter Locking Solutions in Rats: Sodium Citrate as an Alternative to Heparin", Available at https://www.criver.com/sites/default/files/resources/VascularcatheterlockingsolutionsinratsSodiumcitrateasanalternativetoheparin.pdf, 2014.

MacRae et al. "Citrate 4% Versus Heparin and the Reduction of Thrombosis Study (CHARTS)", Clin J Am Soc Nephrol, 2008, pp. 369-374, vol. 3.

Mehta et al. "Regional Citrate Anticoagulation for Continuous Arteriovenous Hemodialysis in Critically Ill Patients", Kidnet International, 1990, pp. 976-981, vol. 38.

Mehta. "Anticoagulation in Severely Ill Patients Treated with Continuous Hemofiltration", Nefrologia, pp. 287-294, vol. 12:4.

Moran et al. "Locking Solutions for Hemodialysis Catheters; Heparin and Citrate—A Position Paper by ASDIN", Seminars in Dialysis, 2008, pp. 490-492, vol. 21:5.

Palm et al. "Prevention of Catheter-Related Infections by a New, Catheter-Restricted Antibiotic Filling Technique", Laboratory Animals, 1991, pp. 142-152, vol. 25.

Polaschegg. "Safety of Concentrated Trisodium Citrate Catheter Locks", Nephrol Dial Transplant, 2008, p. 4075, vol. 23.

Polaschegg et al. "Risks Related to Catheter Locking Solutions Containing Concentrated Citrate", Nephrol Dial Transplant, 2003, pp. 2688-2690, vol. 18.

Power et al. "Sodium Citrate Versus Heparin Catheter Locks for Cuffed Central Venous Catheters: A Single-Center Randomized Controlled Trial", Am J Kidney Dis, 2009, pp. 1034-1041, vol. 53.

Punt et al. "Cardiac Arrest Following Injection of Concentrated Trisodium Citrate", Clinical Nephrology, 2008, pp. 317-318, vol. 69:4.

Purchase et al. "Hemodialysis With a Permcath Kept Open With Streptokinase and Later Citrate in a Heparin-Sensitive Patient", Nephron, 1991, pp. 119-120, vol. 48.

Skofic et al. "Hemodialysis Catheters With Citrate Locking in Critically Ill Patients With Acute Kidney Injury Treated With Intermittent Online Hemotiltration or Hemodialysis", Therapeutic Apheresis and Dialysis, 2009, pp. 327-333, vol. 13:4.

(56) References Cited

OTHER PUBLICATIONS

Stas et al. "Trisodium Citrate 30% vs Heparin 5% as Catheter Lock in the Interdialytic Period in Twin- or Double-Lumen Dialysis Catheters for Intermittent Haemodialysis", Nephrol Dial Transplant, 2001, pp. 1521-1522, vol. 16.
Straaten et al. "Clinical Review: Anticoagulation for Continuous Renal Replacement Therapy—Heparin or Citrate?", Critical Care, 2011, pp. 1-9, vol. 15.
Stranz et al. "Risk of Bacterial Contamination from Citrate Catheter Locks", Seminars in Dialysis, 2009, pp. 704, vol. 22:6.
"The Fresenius Prophylaxis in Catheter Locking", Fresenius, 2013.
Vanholder et al. "Diagnosis, Prevention and Treatment of Haemodialysis Catheter-Related Bloodstream Infections (CRBSI): A Position Statement of European Renal Best Practice (ERBP)", NDT Plus, 2010, pp. 234-246, vol. 3.
Weijmer et al. "Superior Antimicrobial Activity of Trisodium Citrate Over Heparin for Catheter Locking", Nephrol Dial Transplant, 2002, pp. 2189-2195, vol. 17.
Weijmer et al. "Randomized, Clinical Trial Comparison of Trisodium Citrate 30% and Heparin as Catheter-Locking Solution in Hemodialysis Patients", J Am Soc Nephrol, 2005, pp. 2769-2777, vol. 16.
Winnett et al. "Trisodium Citrate 46.7% Selectively and Safely Reduces Staphylococcal Catheter-Related Bacteraemia", Nephrol Dial Transplant, 2008, pp. 3592-3598, vol. 23.
Yon et al. "Sodium Citrate 4% Versus Heparin as a Lock Solution in Hemodialysis Patients with Central Venous Catheters", Am J Health-Syst Pharm., 2013, pp. 131-136, vol. 70.

\* cited by examiner

4% TRISODIUM CITRATE SOLUTION FOR USE AS A CATHETER LOCK SOLUTION

CROSS-REFERENCE TO RELATED APPLICATION

The present application claims priority to U.S. Provisional Patent Application No. 62/561,859, filed Sep. 22, 2017, the contents of which are incorporated by reference herein in their entirety.

BACKGROUND OF THE INVENTION

Field of the Invention

The present invention relates to the maintenance of catheters in a condition that is substantially free of blood and clots. More particularly, the invention relates to the use of a solution of citrate salt to prevent backflow and maintain patency in a catheter lumen.

Description of Related Art

Catheters, particularly intravenous (IV) catheters, may be used for infusing fluid, such as a medication, into a patient or withdrawing fluid, such as blood, from a patient. Catheters may include a lumen or reservoir which contains fluid or medication to be injected into, or removed from, a patient's body. In certain configurations an injection port may be provided with the catheter.

Complications associated with catheters include thrombosis, infection, and clotting. Catheter occlusions will often occur due to thrombotic complications related to the formation of a fibrin sheath within the lumen or at the tip of the catheter. Formation of a fibrin sheath may allow for adherence of bacteria to the interior of the catheter lumen and serve as a locus for catheter related infection.

To reduce problems associated with clotting and thrombus formation, it is common to "lock" intravascular access catheters between successive uses. Locking typically involves first flushing the catheter with saline to remove blood and other substances from the catheter lumen. After the catheter has been flushed, an anti-coagulant solution, typically heparin, is then injected to displace the saline and fill the lumen. The heparin locking solution prevents blood from entering the lumen and actively inhibits clotting and thrombus formation within the lumen.

The heparin lock solution is infused into the catheter lumen immediately after each use, and is left within the catheter until the catheter is accessed again. The heparin lock solution must be withdrawn from the catheter before the next use so that the heparin is not introduced into the body of the patient. In some instances, heparin lock solutions include up to 10,000 units of heparin per catheter lumen. Infusing this amount of heparin into a patient may result in excessive bleeding.

However, even with the use of a traditional heparin lock solution, the catheter can become occluded between uses from coagulation of blood within the catheter. Blood may be present within the catheter because an inadequate volume of heparin was infused within the catheter lumen, the heparin lock solution diffused from the lumen, or residual blood remains in the lumen. This can result in formation of a thrombus with concomitant loss of patency and decreased flow through the catheter lumen.

There remains a need for a catheter lock solution which can provide long-lasting action, increased safety, and without the need for additional applications in between uses of the catheter.

SUMMARY OF THE INVENTION

Accordingly, provided herein is a catheter lock solution that includes a citrate salt. In aspects the citrate salt is a sodium citrate salt. In further aspects, the citrate salt is trisodium citrate.

In aspects, the catheter lock solution further includes an acid. In aspects, the acid is a diluted acid. In some aspects, the diluted acid is diluted hydrochloric acid (HCl).

In aspects, the catheter lock solution includes the citrate salt in an amount between about 3.8% and 4.2% w/v.

In aspects, the lock solution includes the acid in an amount between about 0% and about 0.7% v/v.

In certain aspects, the catheter lock solution includes 4% w/v trisodium citrate, water-for-injection (WFI), and 0.7% v/v 10% HCl.

In certain aspects, the catheter lock solution is free of any additional component having anticoagulant or antimicrobial activity.

Also provided herein is a method of making a catheter lock solution. The method includes the steps of dissolving a citrate salt, preferably trisodium citrate, in WFI and adding a diluted acid, preferably 10% HCl, until the pH of the catheter lock solution is between about 6.4 and about 7.5.

Also provided herein is a catheter lock solution including only trisodium sodium, water-for-injection (WFI), and 10% HCl.

In aspects, the catheter lock solution The catheter lock solution of claim 11, wherein the lock solution includes only between about 3.8% and about 4.2% w/v trisodium citrate, WFI, and between about 0% and about 0.7% v/v of 10% HCl, and has a pH of between about 6.4 and about 7.5.

Also provided herein is a method of making a catheter lock solution. The method includes only the steps of dissolving trisodium citrate in WFI and adding 10% HCl until the pH of the catheter lock solution is between about 6.4 and about 7.5.

Also provided herein is a catheter lock solution including only about 4% w/v trisodium citrate, water-for-injection (WFI), and about 0.7% v/v 10% HCl, the catheter lock solution having a pH of about 7.

Also provided herein are pre-filled syringes including syringes containing a catheter lock solution as described herein.

Also provided herein are catheters including a tube defining a lumen therethrough, at least a portion of the lumen being infused with a catheter lock solution as described herein.

Also provided herein is a method of inhibiting coagulation and microbial activity in a catheter including the steps of providing a catheter including a tube defining a lumen therethrough and infusing into at least a portion of the lumen the catheter lock solution described herein.

DETAILED DESCRIPTION OF THE INVENTION

Figure 1:
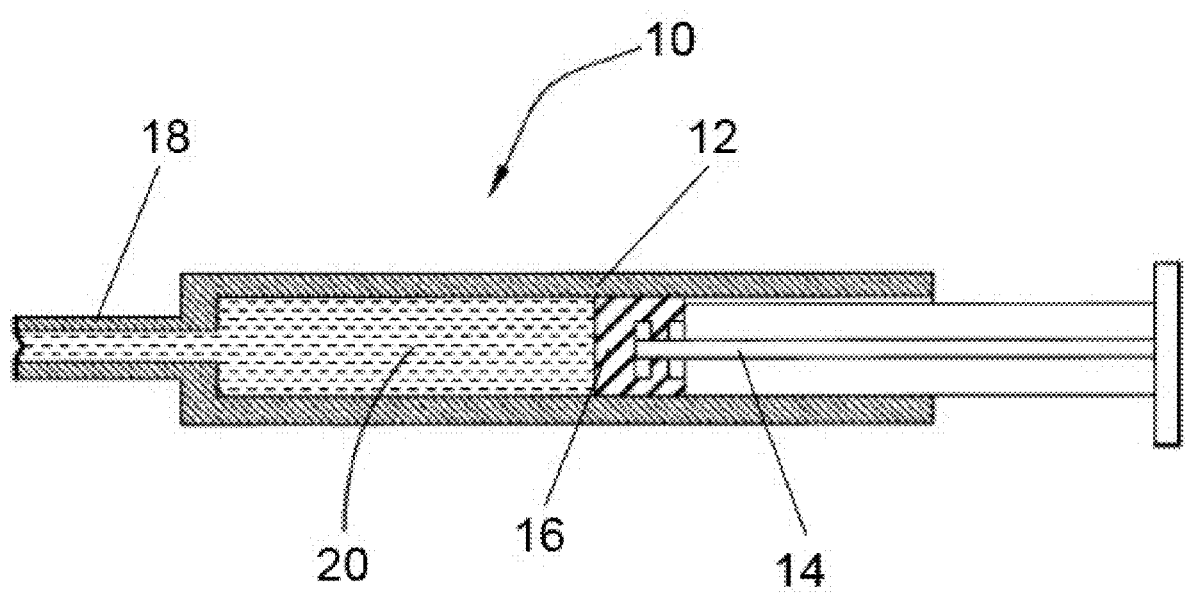
FIG. 1 is a longitudinal cross-section of a pre-filled syringe including the catheter lock solution according to one aspect of the lock solution described herein.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

Provided herein is a catheter lock solution including a citrate salt, a solvent, and a diluted acid. The lock solution described herein provides patency for a catheter and exhibits anticoagulation and antibiotic activity. Without wishing to be bound by the theory, it is believed that the citrate salt acts as an anticoagulant by chelating calcium ($Ca^2$) ions in blood. Calcium ions are necessary for proper functioning of coagulation factors V and VII, which form tenase and prothrombinase complexes in the coagulation cascade. By chelating calcium, the cascade is blocked and coagulation is inhibited.

The lock solution and pre-filled syringe described herein also minimize syringe-induced reflux of blood into an implanted catheter. The lock solution described herein provides significant advantages over typical heparin-based locks, in that adverse events related to use of heparin, such as heparin-induced thrombocytopenia, systemic bleeding complications, and assay interference, can be avoided. In addition, a citrate salt-based lock offers significant cost and time savings over heparin-based solutions. A lock solution as described herein also offers advantages in terms of stable shelf-life, such as at least two years from time of manufacture. Moreover, the use of a pre-filled syringe saves time, improvise sterility, and thus safety, of the product and delivery thereof, and eliminates the likelihood of contamination that can occur during manual filling.

As used herein, the term "lock solution" or "locking solution" refers to a solution that is injected or otherwise infused into a lumen of a catheter with the intention of allowing a substantial portion of the solution to remain in the lumen until it is desired or required to access or re-access the lumen, typically for additional treatment or maintenance. Additional treatment may include, for example, infusion or withdrawal of fluid into/from the lumen of a catheter. The locking solution may be placed into the catheter to provide short or long-term protection. Preferably, the lock solution can remain in the lumen for a desired amount of time lasting to about one week, and in aspects up to about a month. However, the lock solution may be changed on a daily basis, such as during regular care or sterile maintenance of the catheter. The catheter may be changed or refreshed by aspirating the lock solution out of the catheter lumen, and locking the catheter with new catheter lock solution within the catheter for a desired amount of time. Use of a lock solution described herein may prolong the lifetime of the catheter, lengthen the interval between required replacements of the lock solution, and/or inhibit infection in a patient.

The term "catheter" as used herein refers to a tube defining a lumen therethrough that may be inserted into part of the body or provided in communication with a body or other biological culture to deliver a fluid thereto or remove a fluid therefrom. In aspects, the catheter lock solution as described herein may be used to provide anticoagulant activity (inhibit coagulation) and antimicrobial activity in a catheter, such as soft catheter or a hard catheter.

As used herein, the term "anticoagulant activity" refers to inhibition or prevention of blood coagulation.

As used herein, the term "antimicrobial activity" refers to destruction, inhibition, or prevention of the propagation, growth, or multiplication of unwanted micro-organisms, such as aerobic and anaerobic gram-positive and gram-negative bacteria, undulating bacteria, spirochetes, spores, spore-forming micro-organisms, yeasts, fungi, molds, viruses, aerobic organisms, anaerobic organisms, and mycobacteria.

The catheter lock solution as described herein can be used to inhibit microbial activity and coagulation of catheters that are placed into particular parts of the body to allow, for example, drainage of urine from the urinary bladder as in urinary catheterization; drainage of fluid collections; administration of intravenous fluids, medication, or prenatal nutrition; angioplasty; angiography; balloon septostomy; and direct measurement of blood pressure in an artery or vein. While the catheter lock solution as described herein may be used to inhibit microbial activity and coagulation of any catheter, the catheter lock solution may be used to inhibit microbial activity and coagulation of catheters that are used, for example, for hemodialysis and hemofiltration that rely on separate draw and return catheters implanted into a vein to allow extracorporeal treatment of the blood or for peritoneal dialysis, which relies on a single catheter implanted in the peritoneum to permit introduction and withdrawal of dialysate to permit in situ dialysis.

By preventing coagulation within the lumen of a catheter, the citrate salt lock solution as described herein maintains patency within the catheter. As used herein, the term "patency" refers to a catheter being open or unobstructed, for example by clots or fibrin sheaths within the lumen of the catheter.

As described above, the lock solution includes a citrate salt. As used herein, the term "citrate salt" refers to a salt of citric acid. Citric acid is a tricarboxylic acid having the formula $C_6H_8O_7$, and is considered a weak acid. Examples of suitable citrate salts for use in the lock solution described herein are sodium salts and potassium salts. In aspects, the citrate salt is monosodium, disodium, or trisodium citrate. In particular aspects, the citrate salt is trisodium citrate. In some aspects, the trisodium citrate is trisodium citrate dihydrate, a powder form of trisodium citrate that can be dissolved in a solvent.

As described above, it is believed that trisodium citrate functions as an anticoagulant by chelating calcium ($Ca^{2+}$) ions in the blood, disrupting the coagulation cascade. As a lock solution, trisodium citrate acts in two ways to maintain catheter patency. First, the physical presence of the lock solution prevents backflow of blood from the patient into the catheter lumen, reducing the risk of clotting or occlusion of the lumen. Second, to the extent that any blood does backflow into the catheter lumen, by disrupting the coagulation cascade the trisodium citrate prevents clotting in the catheter lumen and at the catheter tip.

The lock solution includes a solvent in which the citrate salt is dissolved. The solvent can be any biocompatible solvent. In aspects, the solvent is water-for-injection (WFI). In aspects, the citrate salt is included in the solvent at a mass per volume concentration of between about 3.8% and about 4.2% weight per volume (w/v), all subranges and values therebetween inclusive. As used herein, the term "about" refers to a difference of ±10% of the value. In aspects, the lock solution is made by dissolving trisodium citrate dihydrate at a mass per volume in WFI of about 4% (w/v).

The lock solution also includes a diluted acid to adjust the pH of the solution. The diluted acid can be any biocompatible organic or inorganic acid. In aspects, the diluted acid is 10% hydrochloric acid (HCl). In aspects, the lock solution includes between about 0 and about 0.7% v/v of diluted acid, all subranges and values therebetween inclusive. In aspects, the lock solution includes between about 0 and about 0.7% v/v of 10% HCl. However, those of skill in the art will understand that the amount of diluted acid can be adjusted to achieve a preferred pH of the lock solution of between about 6.4 and about 7.5.

In particular aspects of the lock solution described herein, the solution includes between about 3.8% and about 4.2% w/v of trisodium citrate in WFI, and the lock solution has a pH of between about 6.4 and about 7.5, and in some aspects between about 6.54 and about 7.25, all subranges therebetween inclusive. In some aspects, the pH of the lock solution when delivered to a syringe during preparation of pre-filled syringes is between about 6.57 and about 7.16, all subranges therebetween inclusive. In some aspects, the pH of the lock solution when delivered to a syringe during preparation of pre-filled syringes is about 6.87.

In aspects, between about 0 and about 0.7% v/v of 10% HCl is included in the lock solution. In some aspects, the lock solution includes about 4% w/v trisodium citrate dihydrate in WFI, and sufficient diluted (e.g., 10%) HCl to provide a lock solution with a pH of about 6.9. In further aspects, the lock solution includes trisodium citrate, WFI, and, optionally, HCl to provide the required pH, and includes no additional anticoagulant or antimicrobial additives. In aspects the catheter lock solution is free of excipients. In some aspects the catheter lock solution is free of alcohols, glycerol, polyethylene glycols, citric acid, and/or polysorbate. In aspects the catheter lock solution is free of any component other than a citrate salt, WFI, and, optionally, HCl.

Also provided herein is an infusion device containing the lock solution as described above. In aspects, the infusion device is a pre-filled syringe including the lock solution as described above. In aspects, the pre-filled syringe includes a distal end, a proximal end, and a barrel therebetween defining a reservoir. The pre-filled syringe includes a plunger at the proximal end and a connector at the distal end configured to connect to a catheter, other needlefree connectors, Y-sites, and the like. In aspects, the connector at the distal end of the pre-filled syringe is a male or female luer connector. With reference to FIG. 1, illustrated is a pre-filled syringe 10 containing a catheter lock solution 20, as described above. The pre-filled syringe includes a barrel 12, plunger rod 14, stopper 16, and luer connection 18. In some aspects, the pre-filled syringe is formed of polypropylene. In particular aspects, one or more of the barrel 12, plunger rod 14, and tip cap (not illustrated) are formed of polypropylene. In aspects, the stopper 16 of the pre-filled syringe is an elastomeric stopper.

In aspects, the pre-filled syringe 10 is designed or configured to reduce or prevent instances of reflux of blood into a catheter at the conclusion of flushing with a lock solution as described herein. In aspects, the pre-filled syringe is configured such that the plunger rod 14 is shorter than a typical plunger rod, such that compression of the stopper 16 following infusion of the lock solution 20 is substantially or completely prevented. In other aspects the stopper 16 is designed or configured such that the nose of the stopper comes into contact with a distal end of the barrel, adjacent the luer 18, and blocks the opening, preventing vacuum and thus reflux of blood into the catheter.

Also provided herein is a method of locking a catheter including the steps of infusing the lock solution as described above into a catheter lumen. In aspects, the method further includes the step of flushing the catheter lumen prior to infusing the lock solution.

In aspects, the method includes the steps of providing a catheter having an interior surface and an exterior surface, and infusing into at least a portion of the interior surface with the catheter locking solution. Preferably, the locking solution is infused into the interior surface such that the interior surface is substantially filled. Non-limiting examples of interior surfaces of the catheter that can be filled with the catheter locking solution described herein include the lumen, related tubing, plungers, caps, and extension sets. Other devices capable of being coated or filled with the catheter locking solution described herein include the inner lumen of vascular access devices, as well as, needle-less access devices. The locking solution can be infused by any conventional method well known to those skilled in the art, such as dipping, spraying, or injecting, for example and without limitation, using the pre-filled syringe as described herein.

When the lock solution described above is infused into the interior surface of the catheter, a sufficient amount of the lock solution can be injected to fill or substantially fill the interior volume/space of the catheter, as well as, any adjacent surfaces or lumens of any attached access device. Alternatively, a volume less than the amount of fluid needed to fill the catheter can be infused into the interior surface. For example, a sufficient amount of lock solution can be infused into the catheter to fill, for example, from 80% to 250% of the internal volume of the catheter, all subranges and percentages therebetween inclusive. In yet another aspect, an amount greater than the internal volume of the catheter can be infused. For example, an amount of the lock solution greater than the internal volume of the catheter can be infused into the lumen. Unlike heparin-based lock solutions, this overflow can be utilized without adverse effects on the clotting system of the patient. The lock solution may be infused or flushed into the catheter between 1 and 1000 times, all subranges and values therebetween inclusive.

The method of locking a catheter, as described above, is effective to prevent backflow of blood from the patient into the lumen of the catheter into which the lock solution is infused or introduced. In addition, the lock solution reduces the occurrence of, or prevents clot formation, maintaining catheter patency.

Also provided herein is a method of making a catheter lock solution as described above. The catheter locking solution can be prepared with simple mixing of the above-identified components at room temperature to provide anticoagulation and antimicrobial activity. In other aspects, the solution is prepared in bulk and loaded into syringes to prepare pre-filled syringes that can be distributed and stored until needed.

Also provided herein is a catheter including a tube defining a lumen therethrough that is pre-filled with the catheter locking solution described above prior to insertion within the patient.

EXAMPLES

Example 1

Figure 2:
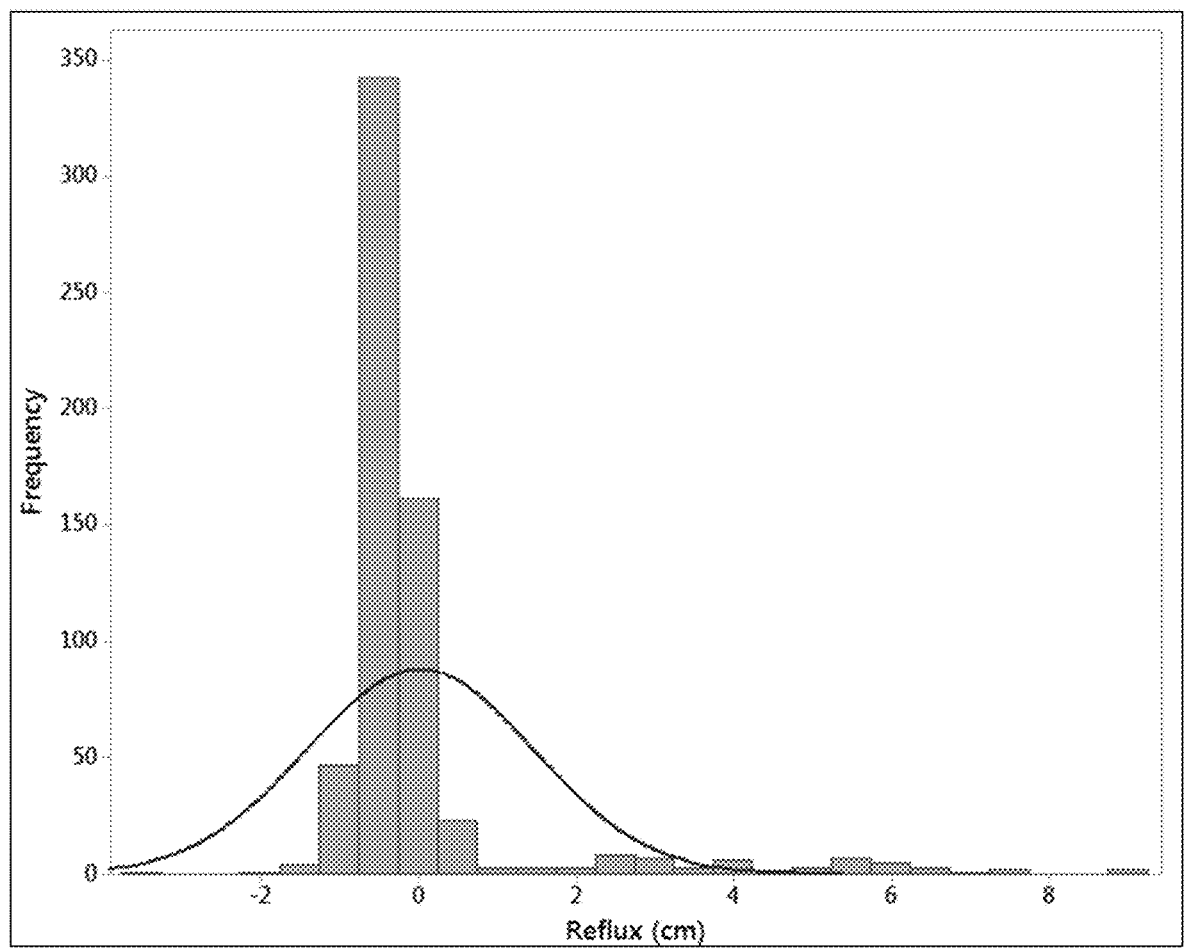
FIG. 2 is a graphical representation of reflux results for a lock solution according to one aspect of the lock solution described herein.

In vitro testing was conducted on samples of the lock solution described herein. Briefly, 5 mL syringes prefilled with sterile 4% sodium citrate compounded at a pH of 6.9 were prepared. Six-hundred and thirty-five samples were tested for reflux with 4 FR, single lumen catheters (Bard, Covington Ga.), and the results are presented in FIG. 2. As can be seen, the average reflux was 0.0±1.4446 cm.

In addition to the above reflux testing, additional samples of sterile 4% sodium citrate compounded at a pH of 6.9 were prepared, and these additional samples underwent accelerated aging at 40° C.±2° C./75% RH±5% RH and real-time aging at 25° C.±2° C./60% RH±5% RH. Accelerated aging results were collected and analyzed at 0, 4, and 6.5 months while real-time aging results were collected and analyzed at 6 months. Results are presented below (average reflux in cm) in Tables 1 and 2.

TABLE 1

Accelerated Aging

| Months | | 5 mL Citrate |
|---|---|---|
| T = 0 | Avg. | −0.552 |
| | St. Dev. | 0.269 |
| T = 4 | Avg. | −0.126 |
| | St. Dev. | 0.558 |
| T = 6.5 | Avg. | −0.212 |
| | St. Dev. | 0.699 |

TABLE 2

Real-Time Aging

| Months | | 5 mL Citrate |
|---|---|---|
| T = 6 | Avg. | −0.394 |
| | St. Dev. | 1.221 |

As can be seen from the above tables, the aged samples demonstrated an average reflux of 0±0.6 cm.

Example 2

Experimental samples were compounded using three lots of different trisodium citrate, each at a pH of 6.9. These samples underwent accelerated aging at 40° C.±2° C./25% RH±5% RH and real-time aging at 25° C.±2° C./40% RH±5% RH. The anticoagulation effectiveness of 4% sodium citrate lock solution on whole blood was determined using the Sonoclot® Coagulation & Platelet Function Analyzer (Sienco Inc., Boulder Colo.), which can calculate the onset of clot formation by monitoring mechanical changes that occur in blood samples during hemostasis. The mechanism is a tubular probe that moves up and down within a blood sample. As the sample progresses through various stages of clotting, electronic circuitry (a transducer) detects increasing resistance. This produces a series of electronic signals that are processed by a microcomputer. The output is the total time of clot formation where the blood is more viscous than initially introduced.

The results of the above testing demonstrated that by preventing clot formation during locking and flushing, a lock solution as described herein is able to maintain the patency of vascular access devices, such as catheters, by preventing/reducing catheter occlusion that may arise from blood clots. Specifically, accelerated aging results were collected and analyzed at 0, 2, 3, 4, 6, and 6.5 months, while real-time aging results were collected and analyzed at 3 and 6 months (Tables 3 and 4, below) and compared to heparin, saline, or blood only (controls).

TABLE 3

Accelerated Aging

| Months | | Citrate | Citrate | Citrate | 10 U/mL Heparin | Saline (Control) | Blood (Control) |
|---|---|---|---|---|---|---|---|
| T = 0 | Avg. | 252.67 | 269.58 | 268.17 | 245.50 | 132.50 | 129.83 |
| | St. Dev. | 80.96 | 77.03 | 69.89 | 26.57 | 13.59 | 7.85 |
| T = 2 | Avg. | 263.75 | 266.83 | 268.50 | 265.75 | 130.92 | 135.17 |
| | St. Dev. | 29.04 | 32.66 | 36.68 | 38.51 | 10.39 | 11.39 |
| T = 3 | Avg. | 204.50 | 205.00 | 207.08 | 280.33 | 127.67 | 122.67 |
| | St. Dev. | 42.63 | 45.13 | 43.51 | 27.17 | 8.35 | 9.34 |
| T = 4 | Avg. | 266.92 | 281.58 | 320.58 | 251.08 | 125.92 | 122.08 |
| | St. Dev. | 84.72 | 67.75 | 100.22 | 30.79 | 8.68 | 7.15 |

TABLE 3-continued

Accelerated Aging

| Months | | Citrate | Citrate | Citrate | 10 U/mL Heparin | Saline (Control) | Blood (Control) |
|---|---|---|---|---|---|---|---|
| T = 6* | Avg. | 237.92 | 254.92 | 250.83 | 229.08 | 121.33 | 122.00 |
| | St. Dev. | 32.74 | 54.82 | 28.11 | 28.91 | 4.74 | 5.31 |
| T = 6.5 | Avg. | 228.42 | 249.25 | 234.83 | 264.67 | 135.42 | 136.17 |
| | St. Dev. | 27.59 | 43.78 | 17.60 | 25.98 | 8.55 | 8.63 |

*= equivalent to two-years of real-time aging

TABLE 4

Real-Time Aging

| Months | | Citrate | Citrate | Citrate | 10 U/mL Heparin | Saline (Control) | Blood (Control) |
|---|---|---|---|---|---|---|---|
| T = 3 | Avg. | 216.92 | 214.83 | 218.92 | 280.33 | 127.67 | 122.67 |
| | St. Dev. | 32.32 | 33.81 | 46.14 | 27.17 | 8.35 | 9.34 |
| T = 6 | Avg. | 247.75 | 227.00 | 241.33 | 229.08 | 121.33 | 122 |
| | St. Dev. | 32.03 | 32.67 | 30.60 | 28.91 | 4.74 | 5.31 |

Figure 3:
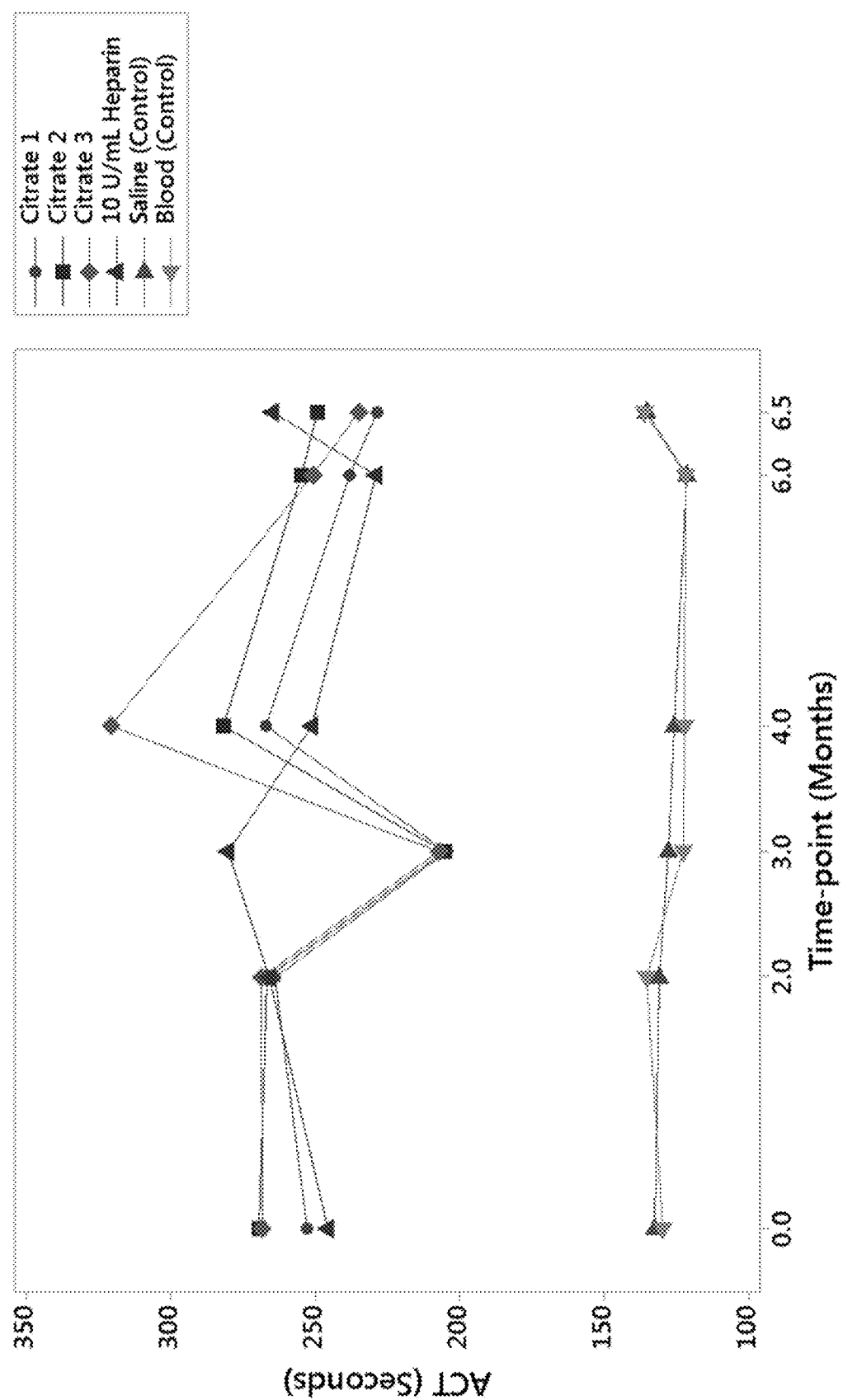
FIG. 3 is a graphical representation of a scatterplot of ACT results for samples according to one aspect of the lock solution described herein that underwent accelerated aging.
Figure 4:
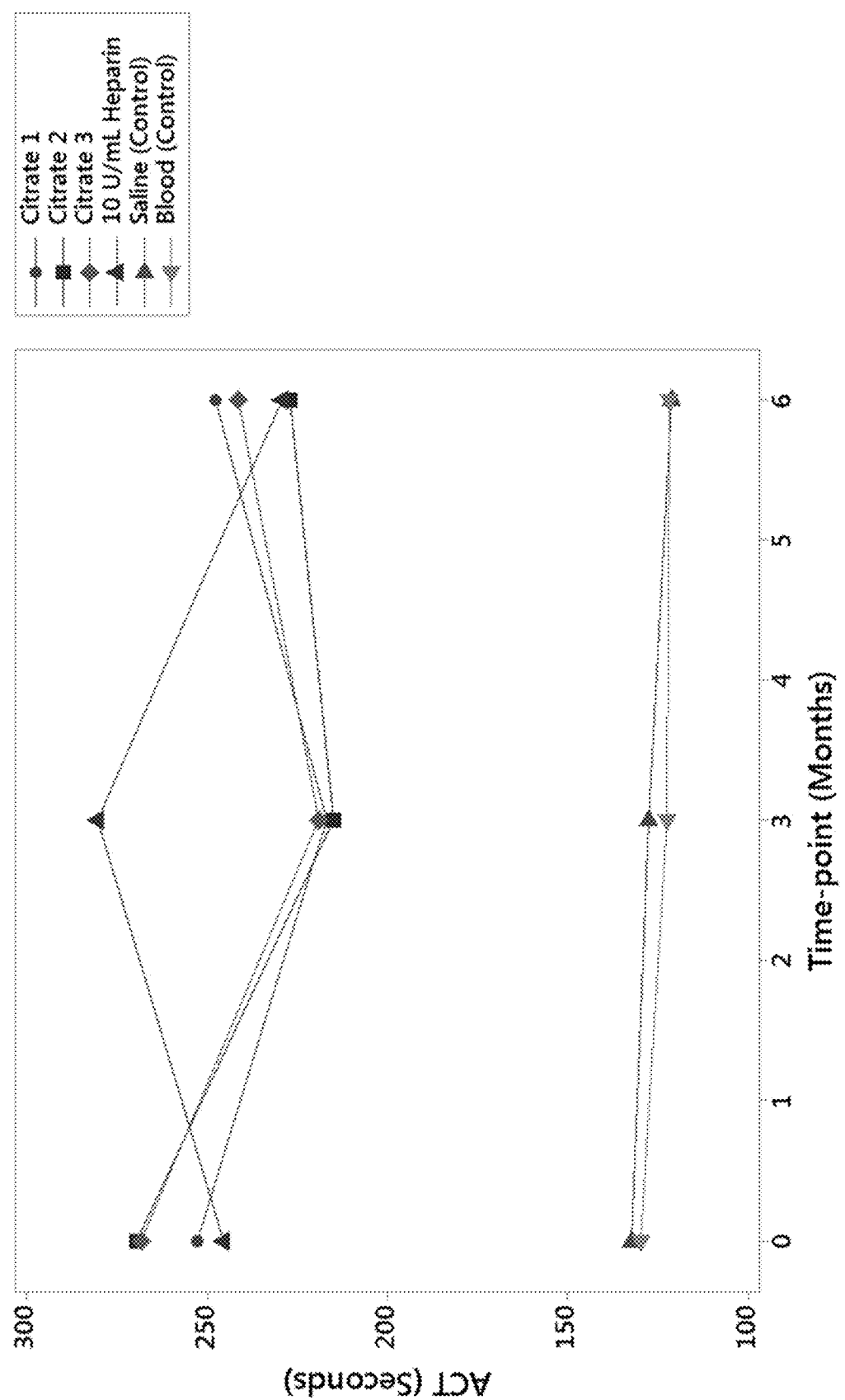
FIG. 4 is a graphical representation of a scatterplot of ACT results for samples according to one aspect of the lock solution described herein that underwent real-time aging.

FIGS. 3 and 4 show scatterplots of results for the accelerated aging (FIG. 3) and real-time aging (FIG. 4) conditions. As can be appreciated, the results demonstrated that a lock solution as described herein exhibits a consistent delayed onset of clotting—activated clotting time (ACT)—over the shelf-life of the product (FIGS. 3 and 4). On average, ACT results were no less than 204.50 seconds (3.41 minutes) and no greater than 320.58 seconds (5.34 minutes) (Tables 1 and 2, above). Within this range lies 10 U/mL heparin lock solution (FIGS. 3 and 4). Thus, it can be concluded that a sodium citrate lock solution, as described herein, can maintain its anticoagulation effectiveness throughout the shelf life of the product. The results also show that the solution demonstrates equivalent anticoagulation and maintenance of catheter patency versus heparin lock solutions, without the adverse effects of heparin use, such as heparin-induced thrombocytopenia, bleeding risks, and systemic anticoagulation. This was further confirmed by performing a general linear model analysis on the ACT results of the sodium citrate lock solution and 10 U/mL heparin lock solution. The analysis, presented below in Table 5, showed that the anticoagulation effectiveness of a 4% sodium citrate solution is equivalent to that of the 10 U/mL prefilled heparin product (p-value of 0.752, no significant difference).

TABLE 5

General Linear Model of Citrate Versus Heparin ACT

| Source | DF | Adj Sum of Squares | Adj Mean Squares | F-Value | P-Value |
|---|---|---|---|---|---|
| Blood Group | 17 | 348440 | 20496.4 | 0.86 | 0.618 |
| Solution Type | 1 | 2230 | 2230.0 | 0.10 | 0.752 |

TABLE 5-continued

General Linear Model of Citrate Versus Heparin ACT

| Source | DF | Adj Sum of Squares | Adj Mean Squares | F-Value | P-Value |
|---|---|---|---|---|---|
| Blood Group * Solution Type | 17 | 404073 | 23769.0 | 25.82 | 0.000 |
| Error | 540 | 497142 | 920.6 | | |
| Total | 575 | 1263984 | | | |

Lastly, the results demonstrated that a sodium citrate lock solution delayed the onset of clots longer than compared to saline (FIGS. 3 and 4). On average, ACT results for saline were no greater than 135.42 seconds (2.26 minutes) compared to a 4% sodium citrate lock solution, which were no less than 204.50 seconds (3.41 minutes) and up to 320.58 seconds (5.34 minutes) (Tables 3 and 4, above).

Example 3

A sodium citrate lock solution, as described herein, demonstrated exceptional stability, and it is believed to have a guaranteed shelf life of 2 years from the date of manufacture. To test this, five batches of 3 mL and 5 mL experimental samples were compounded using three different salt lots, at a pH ranging from 6.8 to 7.0 to evaluate the concentration and pH of the 4% sodium citrate lock solution. As above, these samples underwent accelerated aging at 40° C.±2° C./25% RH±5% RH and real-time aging at 25° C.±2° C./40% RH±5% RH. Accelerated aging results were collected and analyzed at 0, 2, 3, 4, 6, and 6.5 months, while real-time aging results were collected and analyzed at 3 and 6 months. Tables 6 and 7 (below) present results for sodium citrate concentration and Tables 8 and 9 (also below) present results for pH.

TABLE 6

Accelerated Aging, Sodium Citrate Concentration (w/v %)

|   |   | Group 1 (3 mL) | Group 2 (5 mL) | Group 4 (3 mL) | Group 5 (5 mL) | Group 6 (3 mL) | Group 7 (3 mL) | Group 8 (5 mL) |
|---|---|---|---|---|---|---|---|---|
| T = 0 | Avg. | 3.88 | 3.86 | 3.89 | 3.90 | 3.89 | 3.92 | 3.93 |
|   | St. Dev. | 0.02 | 0.02 | 0.02 | 0.03 | 0.04 | 0.01 | 0.02 |
|   | Min | 3.86 | 3.84 | 3.87 | 3.87 | 3.82 | 3.90 | 3.89 |
|   | Max | 3.91 | 3.89 | 3.91 | 3.94 | 3.92 | 3.94 | 3.96 |
| T = 2 | Avg. | 3.98 | 3.97 | 3.96 | 3.96 | 3.97 | 3.96 | 3.95 |
|   | St. Dev. | 0.03 | 0.03 | 0.03 | 0.02 | 0.02 | 0.01 | 0.03 |
|   | Min | 3.93 | 3.93 | 3.94 | 3.94 | 3.94 | 3.95 | 3.92 |
|   | Max | 4.00 | 4.00 | 4.00 | 3.98 | 4.00 | 3.98 | 3.99 |
| T = 3 | Avg. | 3.96 | 3.96 | 3.99 | 3.97 | 3.99 | 3.99 | 3.96 |
|   | St. Dev. | 0.02 | 0.03 | 0.02 | 0.03 | 0.01 | 0.02 | 0.03 |
|   | Min | 3.95 | 3.93 | 3.97 | 3.94 | 3.98 | 3.97 | 3.92 |
|   | Max | 3.99 | 4.01 | 4.02 | 4.01 | 4.01 | 4.03 | 4.00 |
| T = 4 | Avg. | 3.98 | 3.97 | 3.99 | 3.96 | 3.99 | 3.99 | 3.98 |
|   | St. Dev. | 0.01 | 0.03 | 0.01 | 0.03 | 0.02 | 0.01 | 0.01 |
|   | Min | 3.96 | 3.92 | 3.97 | 3.91 | 3.96 | 3.97 | 3.96 |
|   | Max | 3.98 | 4.00 | 4.00 | 3.98 | 4.02 | 4.00 | 3.99 |
| T = 5 | Avg. | 4.05 | 3.99 | 4.03 | 4.01 | 4.02 | 4.02 | 3.99 |
|   | St. Dev. | 0.02 | 0.02 | 0.02 | 0.02 | 0.01 | 0.01 | 0.03 |
|   | Min | 4.02 | 3.96 | 4.00 | 3.97 | 4.01 | 4.00 | 3.95 |
|   | Max | 4.07 | 4.02 | 4.05 | 4.03 | 4.04 | 4.03 | 4.02 |
| T = 6 | Avg. | 4.04 | 4.04 | 4.04 | 4.02 | 4.03 | 4.03 | 3.99 |
|   | St. Dev. | 0.06 | 0.02 | 0.02 | 0.02 | 0.01 | 0.01 | 0.03 |
|   | Min | 3.94 | 4.02 | 4.00 | 4.00 | 4.02 | 4.01 | 3.94 |
|   | Max | 4.08 | 4.08 | 4.06 | 4.05 | 4.05 | 4.04 | 4.01 |
| T = 6.5 | Avg. | 4.01 | 4.01 | 4.04 | 4.00 | 4.03 | 3.99 | 3.99 |
|   | St. Dev. | 0.03 | 0.02 | 0.02 | 0.02 | 0.01 | 0.01 | 0.02 |
|   | Min | 3.96 | 3.98 | 4.01 | 3.99 | 4.02 | 3.98 | 3.97 |
|   | Max | 4.03 | 4.04 | 4.06 | 4.02 | 4.05 | 4.00 | 4.03 |

TABLE 7

Real-Time Aging, Sodium Citrate Concentration (w/v %)

|   |   | Group 1 (3 mL) | Group 2 (5 mL) | Group 4 (3 mL) | Group 5 (5 mL) | Group 6 (3 mL) | Group 7 (3 mL) | Group 8 (5 mL) |
|---|---|---|---|---|---|---|---|---|
| T = 3 | Avg. | 3.98 | 3.99 | 4.01 | 3.99 | 3.99 | 4.04 | 3.99 |
|   | St. Dev. | 0.02 | 0.01 | 0.04 | 0.03 | 0.02 | 0.02 | 0.03 |
|   | Min | 3.95 | 3.98 | 3.95 | 3.96 | 3.97 | 4.00 | 3.97 |
|   | Max | 4.00 | 4.01 | 4.07 | 4.04 | 4.01 | 4.05 | 4.04 |
| T = 6 | Avg. | 3.97 | 3.97 | 3.95 | 3.95 | 3.94 | 3.90 | 3.90 |
|   | St. Dev. | 0.01 | 0.01 | 0.01 | 0.02 | 0.03 | 0.01 | 0.02 |
|   | Min | 3.96 | 3.96 | 3.94 | 3.93 | 3.89 | 3.89 | 3.88 |
|   | Max | 3.99 | 3.98 | 3.97 | 3.99 | 3.96 | 3.91 | 3.92 |

TABLE 8

Accelerated Aging, pH

|   |   | Group 1 (3 mL) | Group 2 (5 mL) | Group 4 (3 mL) | Group 5 (5 mL) | Group 6 (3 mL) | Group 7 (3 mL) | Group 8 (5 mL) |
|---|---|---|---|---|---|---|---|---|
| Bulk | at filler | 6.93 | 6.93 | 6.92 | 6.92 | 7.02 | 6.88 | 6.88 |
| T = 0 | Avg. | 6.93 | 6.96 | 7.07 | 7.08 | 7.00 | 6.86 | 6.86 |
|   | St. Dev. | 0.02 | 0.02 | 0.02 | 0.03 | 0.03 | 0.01 | 0.02 |
|   | Min | 6.90 | 6.93 | 7.04 | 7.02 | 6.96 | 6.83 | 6.83 |
|   | Max | 6.97 | 6.99 | 7.11 | 7.12 | 7.07 | 6.88 | 6.89 |
| T = 2 | Avg. | 6.80 | 6.77 | 6.90 | 7.05 | 7.08 | 6.96 | 6.95 |
|   | St. Dev. | 0.01 | 0.04 | 0.01 | 0.01 | 0.01 | 0.01 | 0.01 |
|   | Min | 6.78 | 6.75 | 6.87 | 7.03 | 7.06 | 6.93 | 6.93 |
|   | Max | 6.82 | 6.91 | 6.92 | 7.07 | 7.10 | 6.97 | 6.96 |
| T = 3 | Avg. | 6.96 | 6.84 | 6.99 | 6.98 | 6.99 | 6.88 | 6.94 |
|   | St. Dev. | 0.07 | 0.01 | 0.02 | 0.01 | 0.02 | 0.02 | 0.03 |
|   | Min | 6.88 | 6.82 | 6.95 | 6.96 | 6.97 | 6.85 | 6.90 |
|   | Max | 7.04 | 6.87 | 7.03 | 7.01 | 7.02 | 6.91 | 7.03 |

TABLE 8-continued

Accelerated Aging, pH

|   |  | Group 1 (3 mL) | Group 2 (5 mL) | Group 4 (3 mL) | Group 5 (5 mL) | Group 6 (3 mL) | Group 7 (3 mL) | Group 8 (5 mL) |
|---|---|---|---|---|---|---|---|---|
| T = 4 | Avg. | 6.79 | 6.96 | 7.05 | 7.01 | 6.94 | 6.82 | 6.79 |
|  | St. Dev. | 0.01 | 0.05 | 0.02 | 0.02 | 0.00 | 0.01 | 0.00 |
|  | Min | 6.77 | 6.87 | 7.01 | 6.98 | 6.94 | 6.80 | 6.78 |
|  | Max | 6.81 | 7.02 | 7.08 | 7.04 | 6.95 | 6.83 | 6.80 |
| T = 5 | Avg. | 6.91 | 6.88 | 6.99 | 6.99 | 7.00 | 6.88 | 6.86 |
|  | St. Dev. | 0.03 | 0.00 | 0.01 | 0.01 | 0.01 | 0.01 | 0.01 |
|  | Min | 6.88 | 6.88 | 6.99 | 6.98 | 6.99 | 6.88 | 6.85 |
|  | Max | 6.98 | 6.89 | 7.00 | 7.00 | 7.02 | 6.90 | 6.89 |
| T = 6 | Avg. | 6.88 | 6.82 | 7.01 | 7.00 | 7.02 | 6.89 | 6.90 |
|  | St. Dev. | 0.03 | 0.01 | 0.01 | 0.01 | 0.01 | 0.02 | 0.01 |
|  | Min | 6.83 | 6.80 | 6.98 | 6.98 | 7.01 | 6.85 | 6.88 |
|  | Max | 6.96 | 6.84 | 7.04 | 7.02 | 7.04 | 6.92 | 6.91 |
| T = 6.5 | Avg. | 6.86 | 6.82 | 6.93 | 6.92 | 7.08 | 6.93 | 6.90 |
|  | St. Dev. | 0.01 | 0.02 | 0.01 | 0.01 | 0.02 | 0.01 | 0.01 |
|  | Min | 6.83 | 6.78 | 6.91 | 6.89 | 7.05 | 6.91 | 6.88 |
|  | Max | 6.88 | 6.84 | 6.94 | 6.93 | 7.13 | 6.95 | 6.92 |

TABLE 9

Real-Time Aging, pH

|   |   | Group 1 (3 mL) | Group 2 (5 mL) | Group 4 (3 mL) | Group 5 (5 mL) | Group 6 (3 mL) | Group 7 (3 mL) | Group 8 (5 mL) |
|---|---|---|---|---|---|---|---|---|
| Bulk | at filler | 6.93 | 6.93 | 6.92 | 6.92 | 7.02 | 6.88 | 6.88 |
| T = 3 | Avg. | 6.93 | 6.89 | 7.00 | 6.97 | 7.01 | 6.91 | 7.07 |
|  | St. Dev. | 0.02 | 0.01 | 0.01 | 0.02 | 0.01 | 0.02 | 0.02 |
|  | Min | 6.89 | 6.87 | 6.98 | 6.95 | 6.98 | 6.86 | 7.04 |
|  | Max | 6.97 | 6.91 | 7.02 | 7.01 | 7.02 | 6.93 | 7.11 |
| T = 6 | Avg. | 6.86 | 6.83 | 6.98 | 6.96 | 6.99 | 6.92 | 6.89 |
|  | St. Dev. | 0.02 | 0.02 | 0.01 | 0.01 | 0.01 | 0.01 | 0.01 |
|  | Min | 6.81 | 6.79 | 6.95 | 6.95 | 6.98 | 6.88 | 6.87 |
|  | Max | 6.88 | 6.85 | 6.99 | 6.97 | 7.00 | 6.94 | 6.90 |

Figure 5:
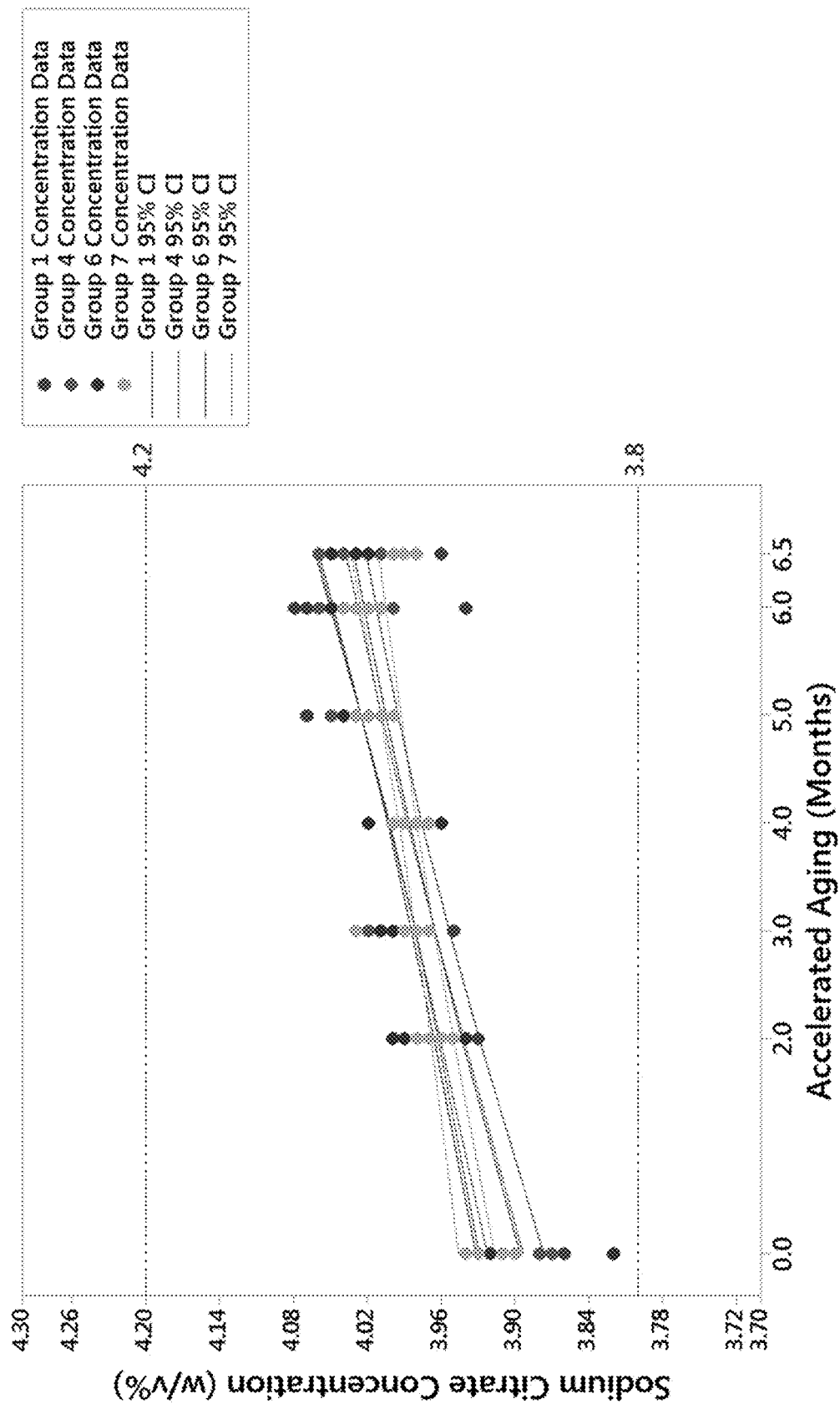
FIG. 5 is a graphical representation of individual sodium citrate concentration data and 95% confidence interval data for 3 mL syringe groups according to one aspect of the lock solution described herein that underwent accelerated aging.
Figure 6:
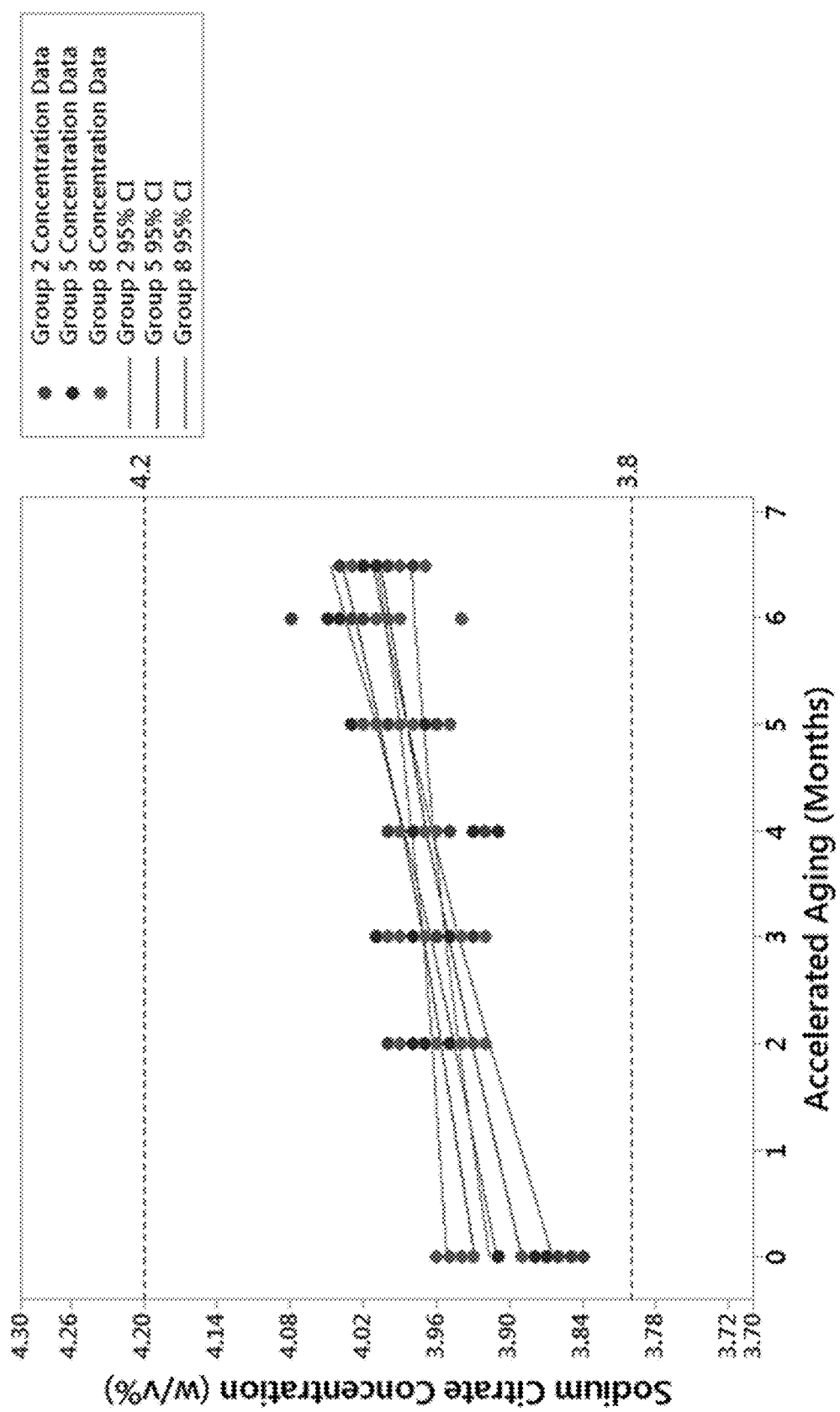
FIG. 6 is a graphical representation of individual sodium citrate concentration data and 95% confidence interval data for 5 mL syringe groups according to one aspect of the lock solution described herein that underwent accelerated aging.
Figure 7:
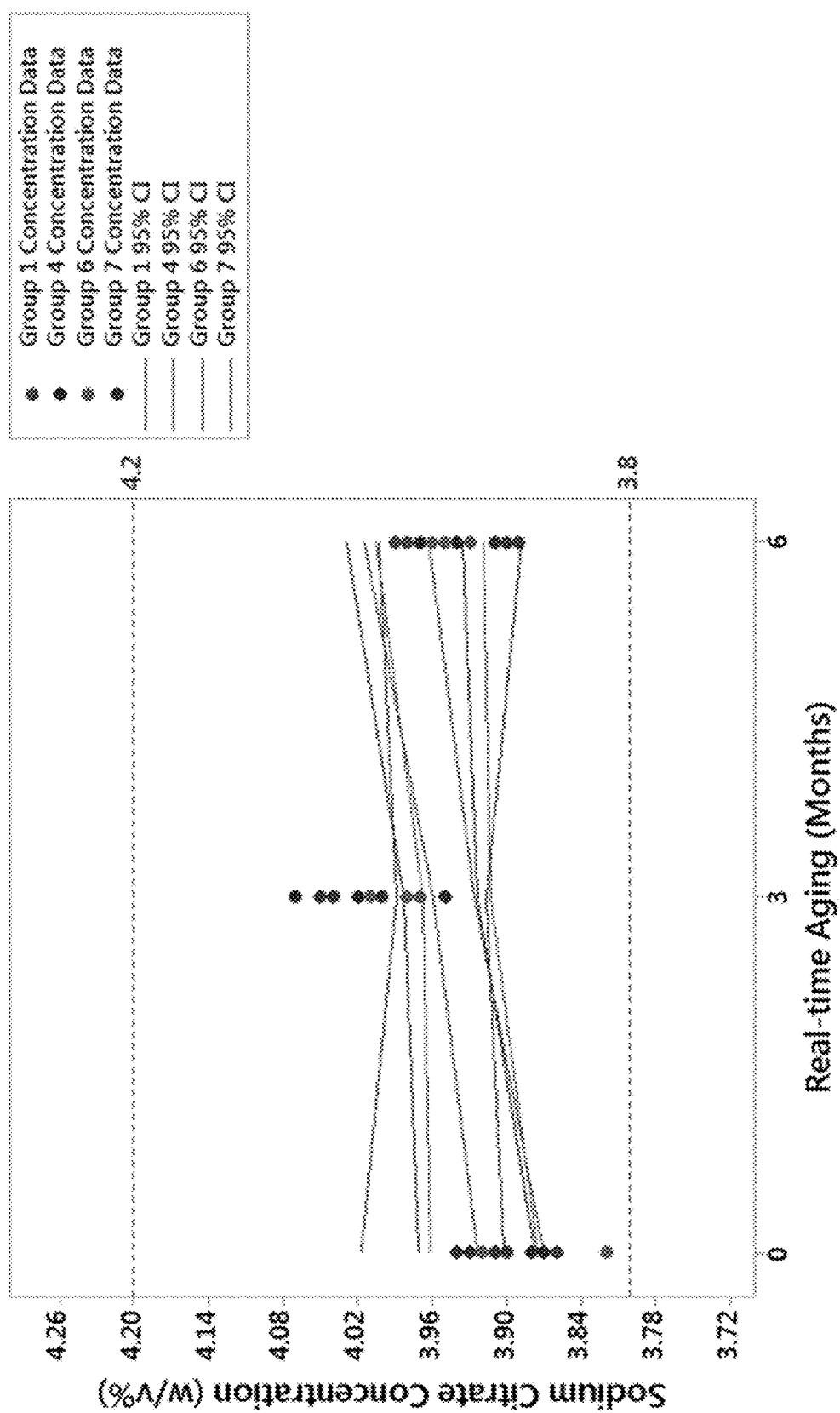
FIG. 7 is a graphical representation of individual sodium citrate concentration data and 95% confidence interval data for 3 mL syringe groups according to one aspect of the lock solution described herein that underwent real-time aging.
Figure 8:
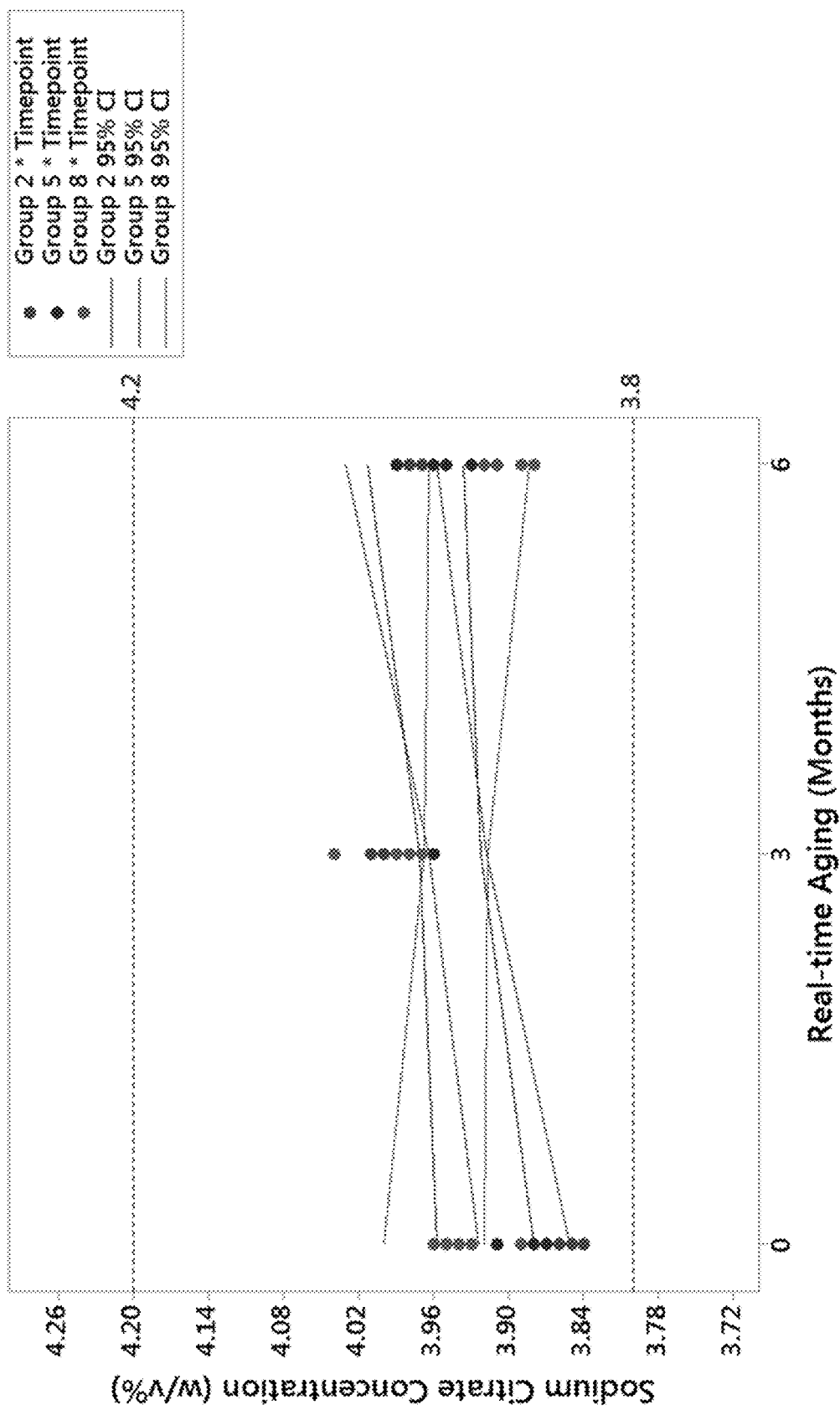
FIG. 8 is a graphical representation of individual sodium citrate concentration data and 95% confidence interval data for 5 mL syringe groups according to one aspect of the lock solution described herein that underwent real-time aging.
Figure 9:
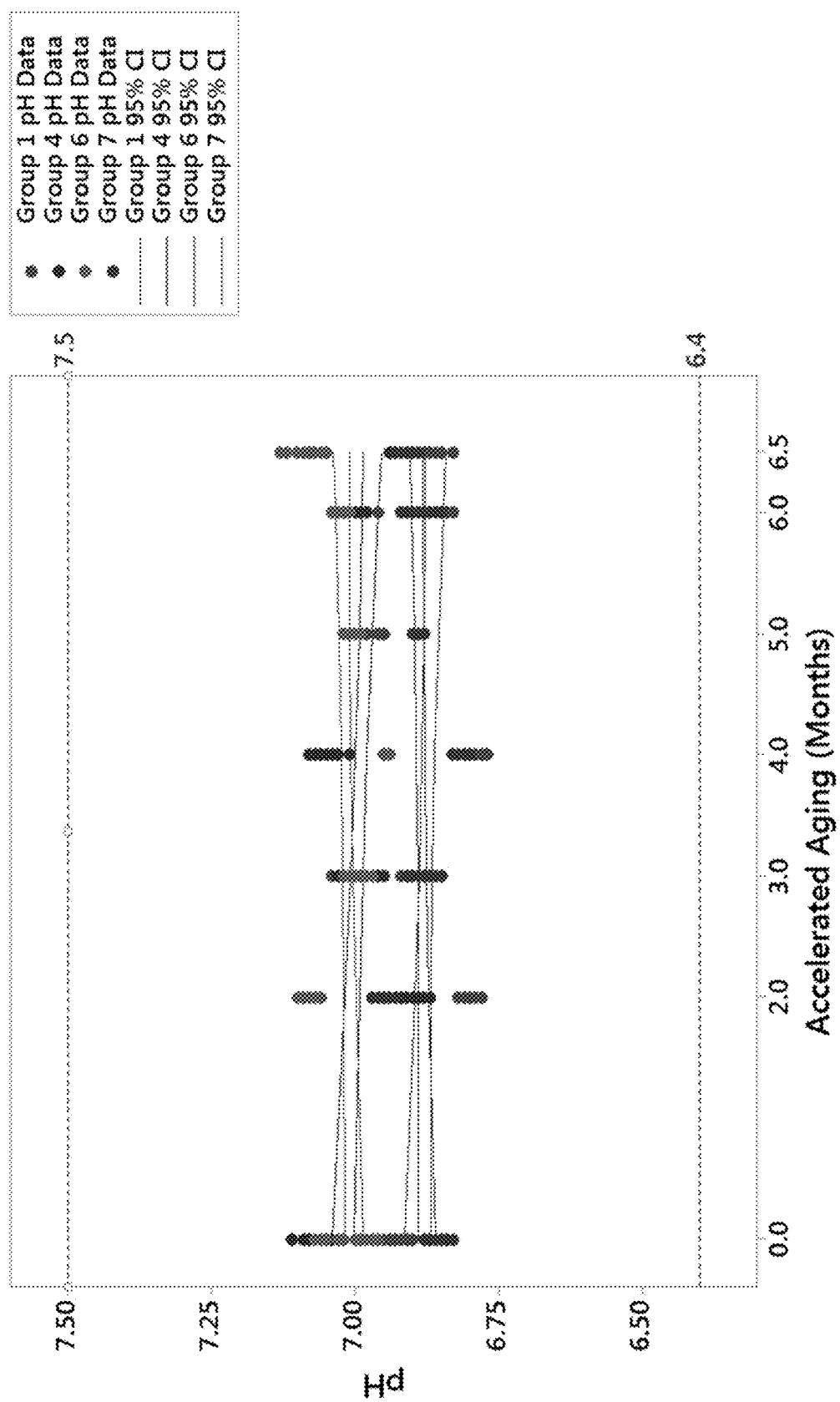
FIG. 9 is a graphical representation of individual pH data and 95% confidence interval data for 3 mL syringe groups according to one aspect of the lock solution described herein that underwent accelerated aging.
Figure 10:
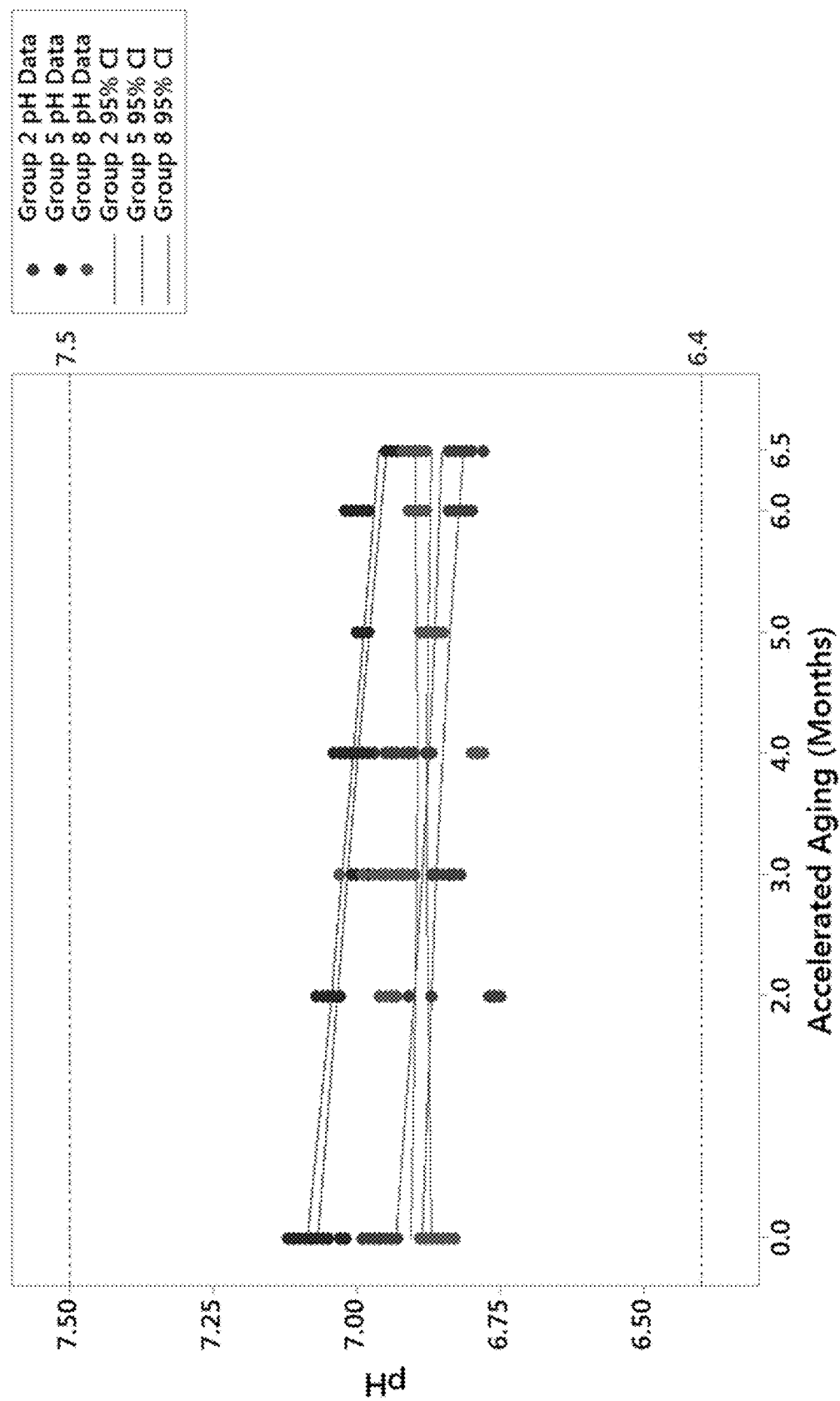
FIG. 10 is a graphical representation of individual pH data and 95% confidence interval data for 5 mL syringe groups according to one aspect of the lock solution described herein that underwent accelerated aging.
Figure 11:
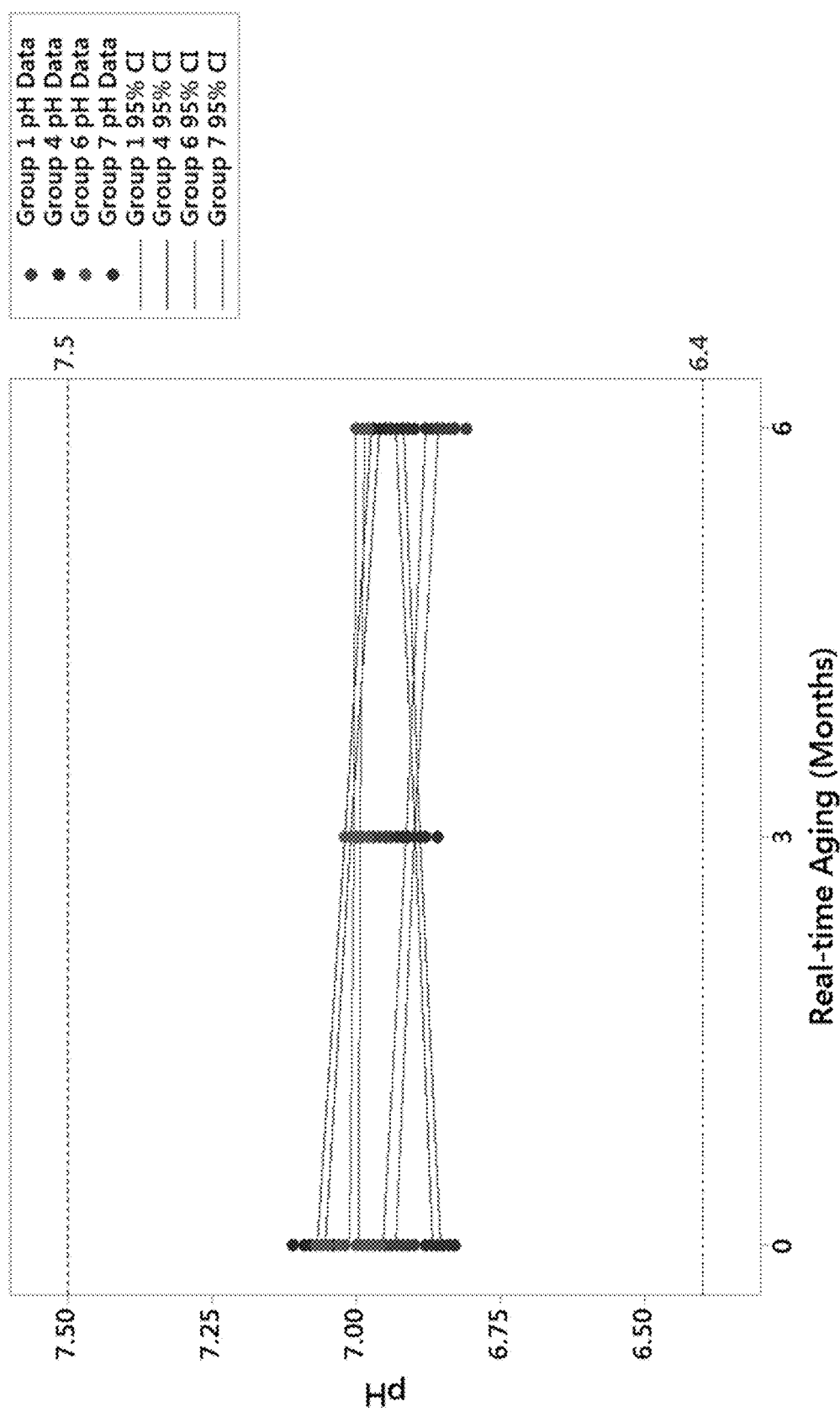
FIG. 11 is a graphical representation of individual pH data and 95% confidence interval data for 3 mL syringe groups according to one aspect of the lock solution described herein that underwent real-time aging.
Figure 12:
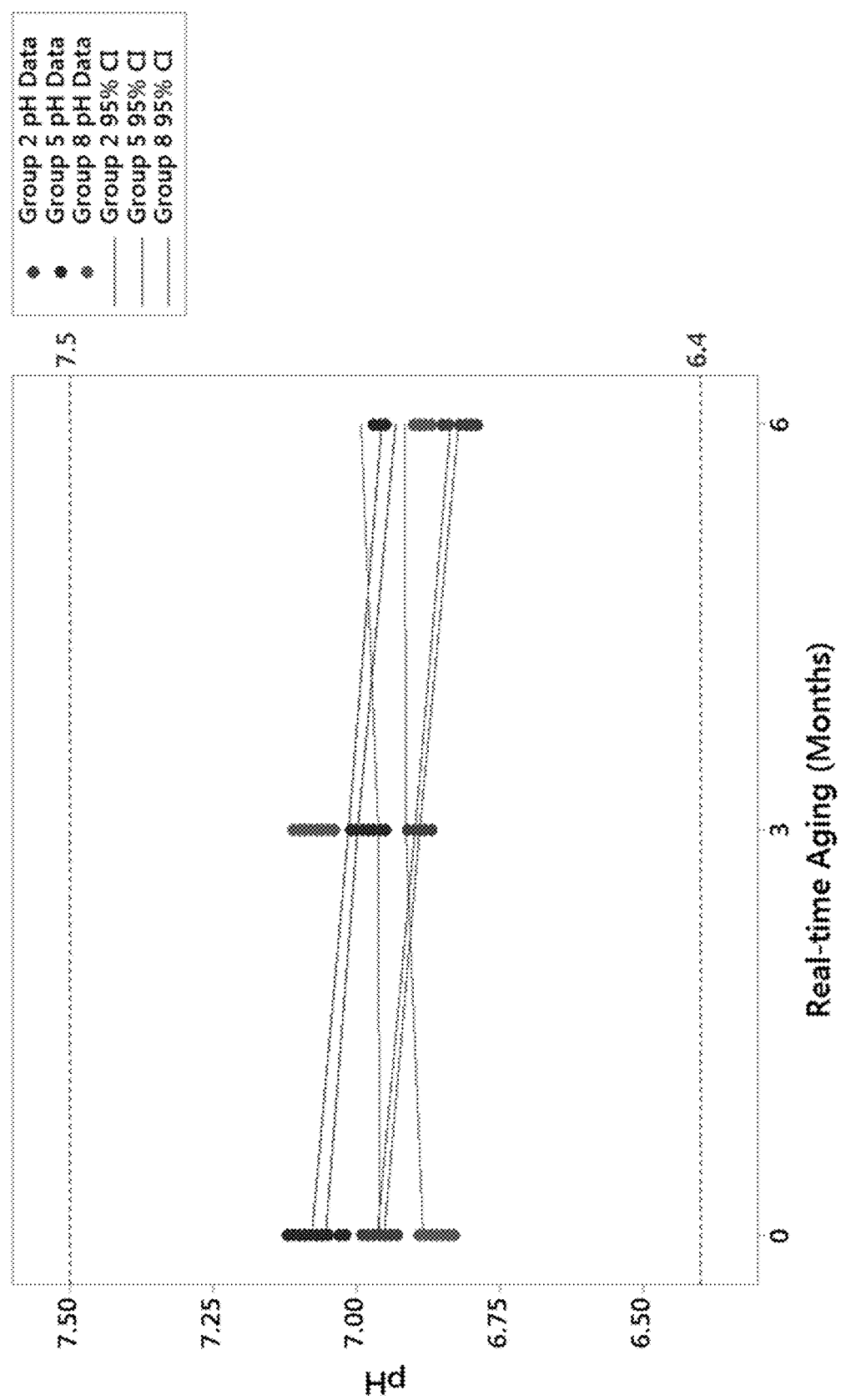
FIG. 12 is a graphical representation of individual pH data and 95% confidence interval data for 5 mL syringe groups according to one aspect of the lock solution described herein that underwent real-time aging.

FIGS. 5-12 show scatterplots of select data from the above tables. FIGS. 5, 6, 9, and 10 show data for the accelerated aging condition (FIGS. 5 and 6 show sodium citrate concentration, FIGS. 9 and 10 show pH), and FIGS. 7, 8, 11, and 12 show data for the real-time aging condition (FIGS. 7 and 8 show sodium citrate concentration, FIGS. 11 and 12 show pH).

As the data shows, throughout the two-year equivalent time point (6.01 months for 3 mL syringes and 5.04 months for 5 mL syringes) and beyond (6.5 months), the results of the five batches demonstrated that the solution concentration and pH was within the corresponding USP38-NF33 specification interval for anticoagulant 4% sodium citrate, 3.8-4.2% w/v (FIGS. 5-8), and pH 6.4-7.5 (FIGS. 9-12), respectively.

While the present invention has been described in terms of the above detailed description, those of ordinary skill in the art will understand that alterations may be made within the spirit of the invention. Accordingly, the above should not be considered limiting, and the scope of the invention is defined by the appended claims.

What is claimed is:

1. A catheter lock solution comprising:
   about 3.8% w/v to about 4.2% w/v, based on a total volume of the lock solution, of trisodium citrate;
   water for injection; and
   about 0.1% to about 0.7% v/v, based on the total volume of the lock solution, of 10% HCl,
   wherein a pH of the catheter lock solution is between about 6.4 and about 7.5, and
   wherein the catheter lock solution includes no additional anticoagulant or antimicrobial additives.

2. The catheter lock solution of claim 1, wherein the trisodium citrate comprises trisodium citrate di-hydrate.

3. The catheter lock solution of claim 1, wherein the catheter lock solution comprises about 4% w/v, based on the total volume of the lock solution, trisodium citrate, water-for-injection (WFI), and about 0.7% v/v, based on the total volume of the lock solution, of 10% HCl.

4. The catheter lock solution of claim 1, wherein the catheter lock solution is free of excipients.

5. The catheter lock solution of claim 1, wherein the catheter lock solution is free of paraben, alcohol, glycerol, polyethylene glycol, citric acid, and polysorbate.

6. A method of making the catheter lock solution of claim 1, consisting of dissolving the trisodium citrate in water-for-injection (WFI) and, optionally, adding an acid until the pH of the catheter lock solution is between about 6.4 and about 7.5.

7. A catheter lock solution consisting of:
   about 4% w/v, based on a total volume of the lock solution, trisodium citrate;
   water-for-injection (WFI); and
   about 0.7% v/v, based on a total volume of the lock solution, of 10% HCl,
   wherein the catheter lock solution has a pH of about 7, wherein the catheter lock solution is free of additional anticoagulant or antimicrobial additives.

8. A pre-filled syringe comprising a syringe containing the catheter lock solution of claim 7.

9. A catheter comprising a tube defining a lumen therethrough, wherein at least a portion of the lumen is infused with the catheter lock solution of claim 7.

10. A method of inhibiting coagulation and microbial activity in a catheter comprising:
   providing a catheter comprising a tube defining a lumen therethrough; and
   infusing, into at least a portion of the lumen of the catheter, the catheter lock solution of claim 7.

* * * * *